United States Patent
Rao et al.

(10) Patent No.: US 10,492,829 B2
(45) Date of Patent: Dec. 3, 2019

(54) REUSABLE DELIVERY DEVICES

(71) Applicant: Boston Scientific Scimed, Inc., Maple Grove, MN (US)

(72) Inventors: Doreen S Rao, Sudbury, MA (US); James M Goddard, Pepperell, MA (US); Joshin Sahadevan, Karnataka (IN); Gururaju Chikkaraju, Karnataka (IN); Michael S. H. Chu, Brookline, MA (US); Kenneth W Adams, Acton, MA (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 828 days.

(21) Appl. No.: 14/817,753

(22) Filed: Aug. 4, 2015

(65) Prior Publication Data

US 2016/0038179 A1     Feb. 11, 2016

Related U.S. Application Data

(60) Provisional application No. 62/033,876, filed on Aug. 6, 2014.

(51) Int. Cl.
*A61B 17/34*     (2006.01)
*A61B 17/00*     (2006.01)
(Continued)

(52) U.S. Cl.
CPC .... *A61B 17/3468* (2013.01); *A61B 17/00234* (2013.01); *A61B 17/06109* (2013.01);
(Continued)

(58) Field of Classification Search
CPC ....... A61F 2002/0072; A61B 17/06109; A61B 17/3468; A61B 2017/00336;
(Continued)

(56) References Cited

U.S. PATENT DOCUMENTS

| | | | |
|---|---|---|---|
| 5,846,181 A | 12/1998 | Heckele et al. | |
| 5,899,909 A | * 5/1999 | Claren | A61B 17/04 606/118 |

(Continued)

FOREIGN PATENT DOCUMENTS

| | | |
|---|---|---|
| CN | 1444465 A | 9/2003 |
| EP | 1139883 B1 | 11/2008 |

(Continued)

OTHER PUBLICATIONS

International Preliminary Report on Patentability for PCT Application No. PCT/US2015/043762, dated Feb. 16, 2017, 12 pages.
(Continued)

*Primary Examiner* — Thaddeus B Cox
(74) *Attorney, Agent, or Firm* — Brake Hughes Bellermann LLP

(57) ABSTRACT

According to an aspect, a medical device may include a needle member, and a handle coupled to the needle member. The handle may define a track portion. The medical device may also include a pusher member having a sheath disposed around a portion of the needle member, and an extension member being movably coupled to the track portion of the handle such that the pusher member is configured to move from a first position to a second position during a surgical procedure. The pusher member may be removable from the handle. The sheath may define a slot, and the pusher member may be removable from the needle member through the slot.

20 Claims, 22 Drawing Sheets

(51) Int. Cl.
*A61F 2/00* (2006.01)
*A61B 17/06* (2006.01)
*A61B 90/00* (2016.01)

(52) U.S. Cl.
CPC ............... *A61B 2017/0046* (2013.01); *A61B 2017/00336* (2013.01); *A61B 2017/00469* (2013.01); *A61B 2017/00477* (2013.01); *A61B 2017/00805* (2013.01); *A61B 2090/0813* (2016.02); *A61F 2002/0072* (2013.01); *A61F 2220/0025* (2013.01)

(58) Field of Classification Search
CPC .. A61B 2017/00805; A61B 2017/0046; A61B 17/3496; A61B 2090/0813
USPC .............................................. 600/29, 30, 37
See application file for complete search history.

(56) References Cited

U.S. PATENT DOCUMENTS

| | | | |
|---|---|---|---|
| 6,530,933 B1* | 3/2003 | Yeung | A61B 17/0401 128/898 |
| 2004/0102804 A1 | 5/2004 | Chin et al. | |
| 2005/0061334 A1* | 3/2005 | Krueger | A61B 17/24 128/897 |
| 2005/0131392 A1 | 6/2005 | Chu et al. | |
| 2006/0205996 A1* | 9/2006 | Presthus | A61B 5/1076 600/29 |
| 2013/0060261 A1* | 3/2013 | Ostrovsky | A61B 17/0469 606/139 |
| 2013/0253260 A1 | 9/2013 | Lund et al. | |

FOREIGN PATENT DOCUMENTS

| | | |
|---|---|---|
| FR | 2129116 A5 | 10/1972 |
| JP | 2003527146 A | 9/2003 |
| JP | 2005118548 A | 5/2005 |
| JP | 2010012281 A | 1/2010 |
| JP | 2012120751 A | 6/2012 |
| WO | 2007004531 A1 | 1/2007 |
| WO | 2016022649 A1 | 2/2016 |

OTHER PUBLICATIONS

International Search Report and Written Opinion for PCT Application No. PCT/US2015/043762, dated Jan. 5, 2016, 18 pages.
Invitation to Pay Add'l Fees and Partial Search Rpt for PCT Application No. PCT/US2015/043762, dated Oct. 8, 2015, 6 pages.
Office Action for Japanese Application No. 2017-506721, dated Mar. 5, 2018, 5 pages.

* cited by examiner

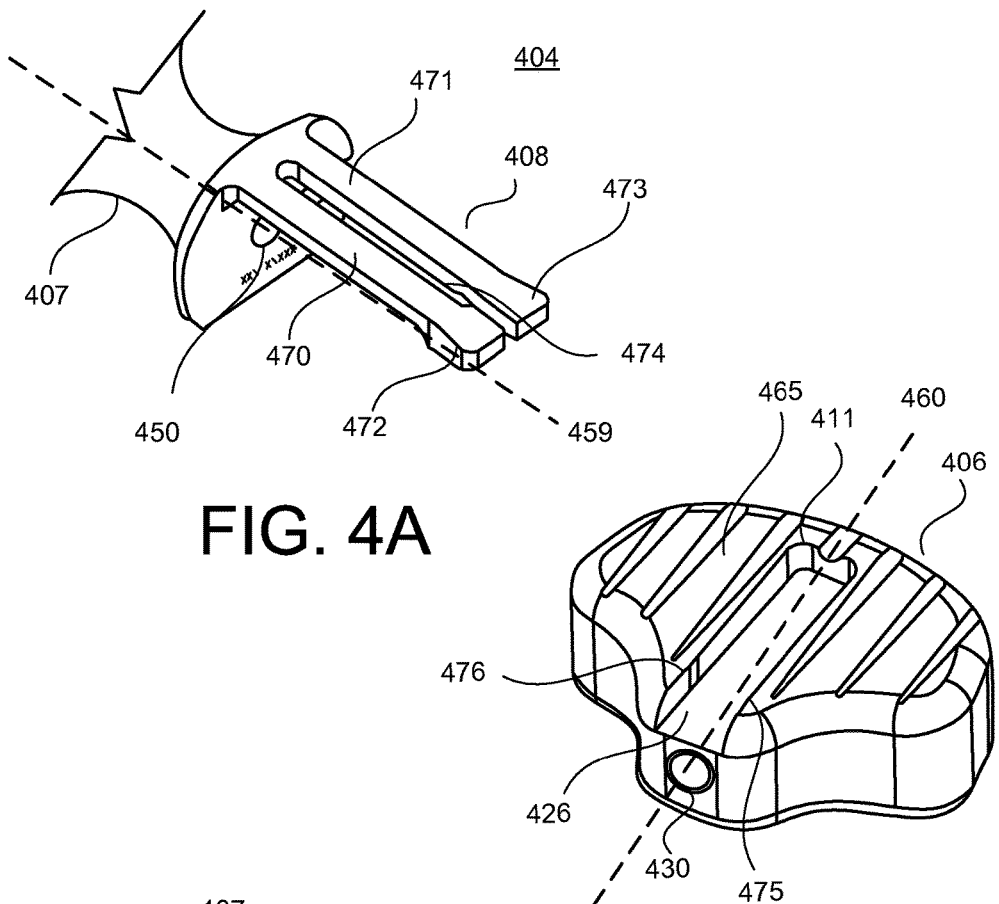
FIG. 4A
FIG. 4B
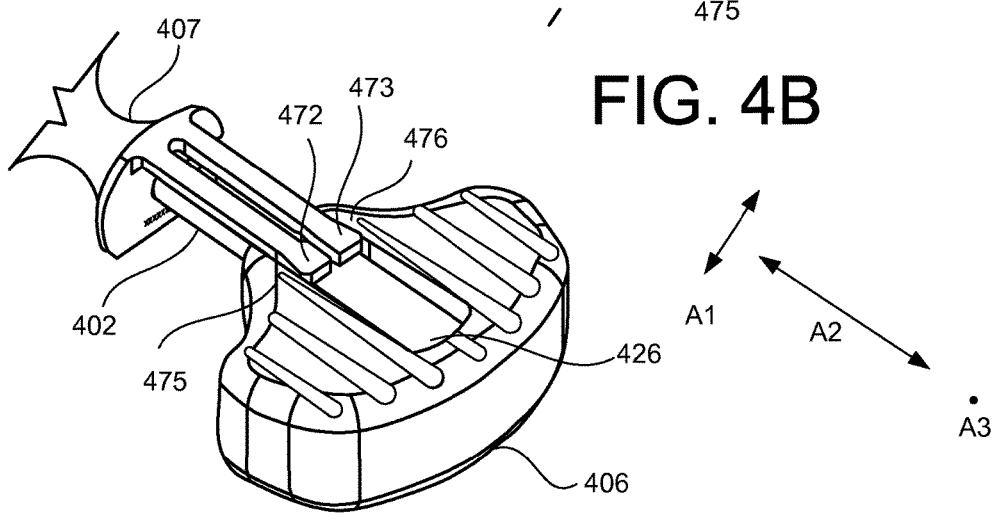
FIG. 4C

REUSABLE DELIVERY DEVICES

CROSS-REFERENCE TO RELATED APPLICATION

This application is a Nonprovisional of, and claims priority to, U.S. Patent Application No. 62/033,876, filed on Aug. 6, 2014, entitled "REUSABLE DELIVERY DEVICES", which is incorporated by reference herein in its entirety.

TECHNICAL FIELD

This disclosure relates generally to medical devices, surgical procedures, and techniques for assembling and disassembling the medical devices, and particularly reusable medical devices for delivering implants, and methods of assembling and disassembling the reusable medical devices.

BACKGROUND

Most conventional sling delivery devices are designed for single-use. For example, after a delivery device is used within a surgical procedure for implanting a sling, the single-use sling delivery device is discarded. For example, during the surgical procedure, bodily fluids or other contaminating substances may be embedded within components or between components of the delivery device, which may be relatively difficult to clean and sterilize. In particular, conventional sling delivery devices may be constructed in a manner that does not permit its components to be easily disassembled, properly sterilized, and then re-assembled to be used in a subsequent surgical procedure. As such, the re-processing of single-use sling deliver devices may pose health and safety hazards to the patient and the operator. However, despite these hazards, the re-processing of single-use sling delivery devices may be relatively common in certain parts of the world.

SUMMARY

According to an aspect, a medical device may include a needle member, and a handle coupled to the needle member. The handle may define a track portion. The medical device may also include a pusher member having a sheath disposed around a portion of the needle member, and an extension member being movably coupled to the track portion of the handle such that the pusher member is configured to move from a first position to a second position during a surgical procedure. The pusher member may be removable from the handle. The sheath may define a slot, and the pusher member may be removable from the needle member through the slot.

According to some aspects, the medical device may include one or more of the following features (or any combination thereof). The track portion may define a recess. At least a portion of the extension member may be disposed within the recess. The track portion may include at least one protrusion. The track portion may include a tapered portion. The pusher member may be removable from the handle based on a rotation of the pusher member. The extension member may define a slot. The pusher member may be removable from the handle based on a rotation through the slot of the extension member. The extension member may include a flexible lip. The pusher member may be removable from the handle based on a force applied to the flexible lip. The pusher member may be removable from the handle by applying a force to the pusher member. The force may be greater than a force used to move the pusher member from the first position to the second position during the surgical procedure. The extension member may define a first extension member and a second extension member. The extension member may define an opening between the first extension member and the second extension member. The slot may extend in a direction parallel to a longitudinal axis of the pusher member. The pusher member may include a handle portion. The handle portion may be disposed between the extension member and the sheath. The handle portion may be disposed around the portion of the needle member. The sheath and the handle portion may define the slot. The handle portion may include a proximal end portion. The extension member may extend from a surface of the proximal end portion of the extension member. The handle may define a first opening, a second opening, and a lumen between the first opening and the second opening. A proximal end portion of the needle member may extend into the lumen through the first opening. The medical device may include a securing member configured to be inserted into the lumen through the second opening of the handle. The securing member may be configured to be removably coupled to the proximal end portion of the needle member. The proximal end portion of the needle member may include a first threaded fastener portion and the securing member may include a second threaded fastener portion.

According to an aspect, a medical device may include a needle member, and a handle coupled to the needle member. The handle may define a track portion. The medical device may include a pusher member having a sheath disposed around a portion of the needle member and an extension member being movably coupled to the track portion of the handle such that the pusher member is configured to move from a first position to a second position during a surgical procedure. The pusher member may be removable from the handle. The sheath may define a slot. The pusher member may be removable from the needle member through the slot.

According to some aspects, the medical device may include one or more of the following features (or any combination thereof). The track portion may define a recess. At least a portion of the extension member may be disposed within the recess. The track portion may include at least one protrusion. The track portion may include a tapered portion. The pusher member may be removable from the handle based on a rotation of the pusher member. The extension member may define a slot. The pusher member may be removable from the handle based on a rotation through the slot of the extension member. The extension member may include a flexible lip. The pusher member may be removable from the handle based on a force applied to the flexible lip. The pusher member may be removable from the handle by applying a force to the pusher member. The force may be greater than a force used to move the pusher member from the first position to the second position during the surgical procedure. The extension member may define a first extension member and a second extension member. The extension member may define an opening between the first extension member and the second extension member. The slot may extend in a direction parallel to a longitudinal axis of the pusher member. The pusher member may include a handle portion. The handle portion may be disposed between the extension member and the sheath. The handle portion may be configured to be disposed around the portion of the needle member. The sheath and the handle portion may define the slot. The handle portion may include a proximal end portion. The extension member may extend from a surface of the proximal end portion of the extension member.

According to an aspect, a medical device may include a needle member having a proximal end portion, and a handle coupled to the proximal end portion of the needle member. The handle may define a track portion. The medical device may include a pusher member. The pusher member may include a sheath disposed around a portion of the needle member, a handle portion disposed around the portion of the needle member, and an extension member movably coupled to the track portion of the handle such that the pusher member is configured to move from a first position to a second position during a surgical procedure. The pusher member may be removable from the handle when not used within the surgical procedure. The sheath and the handle portion may define a slot. The pusher member may be removable from the needle member through the slot.

According to some aspects, the medical device may include one or more of the following features (or any combination thereof). The track portion may define a recess. At least a portion of the extension member may be disposed within the recess. The handle portion may include a proximal end portion. The extension member may extend from a surface of the proximal end portion of the extension member. The slot may extend in a direction parallel to a longitudinal axis of the pusher member.

According to an aspect, a medical device may include a needle member having a proximal end portion, and a handle defining a first opening, a second opening, and a lumen between the first opening and the second opening. The proximal end portion of the needle member may extend into the lumen through the first opening. The medical device may include a securing member configured to be inserted into the lumen through the second opening of the handle. The securing member may be configured to be removably coupled to the proximal end portion of the needle member. The medical device may include a pusher member including a sheath disposed around a portion of the needle member. The pusher member may be configured to move from a first position to a second position in relation to the handle during a surgical procedure.

According to some aspects, the medical device may include one or more of the following features (or any combination thereof). The pusher member may be removably coupled to the handle. The handle may define a track portion. The pusher member may include an extension member. The extension member may be configured to be movably coupled to the track portion. The proximal end portion may include a first threaded fastener portion and the securing member may include a second threaded fastener portion.

According to some aspects, the methods may include methods for assembling/de-assembling a medical device having a pusher member, handle, and needle member. In some examples, the pusher member may include an extension member. A method may include decoupling the pusher member from the handle. In some examples, the pusher member may be de-coupled from the handle by rotating the pusher member. The rotation of the pusher member may cause the pusher member to be de-coupled from the handle. In some examples, the pusher member may rotate off the handle through a slot defined on the pusher member. In some examples, the pusher member may be de-coupled from the handle by applying a pressure to a portion of the extension member of the pusher member. In some examples, the pusher may be de-coupled from the handle by applying a distal force greater than the force used to move the pusher member during the surgical procedure. The method may further include de-coupling the pusher member from the needle member. For example, the pusher member may define a slot or opening on the side of the pusher member, and the pusher member may be removed from the needle member through the slot or opening a direction different than an axis that defines the movement of the pusher during the medical procedure. Optionally, the method may further include de-coupling the needle member from the handle. In some examples, the needle member and the handle may be coupled according to a fastener mechanism (e.g., male/female threaded members). As such, by rotating one of the needle member and the handle, the needle member and the handle may be separated from each other. The method may include sterilizing the separated components of the medical device. Then, the separated components may be reassembled to be re-used in a subsequent medical produced.

The method may include decoupling a securing member from the needle member. For example, the proximal end portion of the needle member may extend through a first opening of the handle into a cavity defined by the handle, the securing member may extend through a second opening of the handle into the cavity of the handle, and the securing member and the proximal end portion of the needle member may be removably coupled. In some examples, the securing member may be rotated to decouple the securing member from the proximal end portion of the needle member. The method may further include removing the needle member from the handle. For example, the proximal end portion of the needle member may move out of the first opening of the handle. The method may further include removing the pusher member from the handle. For example, the pusher member may be slide over the proximal end portion of the needle member. In this manner, the pusher member, the needle member, and the handle may be separated. Then, the medical device may be sterilized such that the medical device can be re-assembled and then used in a subsequent medical procedure.

BRIEF DESCRIPTION OF THE DRAWINGS

FIG. 4A illustrates a pusher member according to another aspect.

FIG. 4B illustrates a handle according to another aspect.

FIG. 4C illustrates the pusher member and the handle of FIGS. 4A and 4B according to an aspect.

DETAILED DESCRIPTION

Detailed embodiments are disclosed herein. However, it is understood that the disclosed embodiments are merely examples, which may be embodied in various forms. Therefore, specific structural and functional details disclosed herein are not to be interpreted as limiting, but merely as a basis for the claims and as a representative basis for teaching one skilled in the art to variously employ the embodiments in virtually any appropriately detailed structure. Further, the terms and phrases used herein are not intended to be limiting, but to provide an understandable description of the invention.

The terms "a" or "an," as used herein, are defined as one or more than one. The term "another," as used herein, is defined as at least a second or more. The terms "including" and/or "having", as used herein, are defined as comprising (i.e., open transition). The term "coupled" or "moveably coupled," as used herein, is defined as connected, although not necessarily directly and mechanically.

The term patient may hereafter be used for a person who benefits from the medical device or the methods disclosed in the present application. For example, the patient can be a person whose body is operated through the medical device or the method disclosed by the present invention. For example, in some aspects, the patient may be a human female, a human male, or any other mammal.

The terms proximal and distal described in relation to various devices, apparatuses, and components as discussed in the subsequent text of the present application are referred with a point of reference. The point of reference, as used in this description, is a perspective of an operator. The operator may be a surgeon, a physician, a nurse, a doctor, a technician, and the like who may perform the procedure and operate the medical device as described in the present invention. The term proximal refers to an area or portion that is closer or closest to the operator during a surgical procedure. The term distal refers to an area or portion that is farther or farthest from the operator.

Figure 1A:
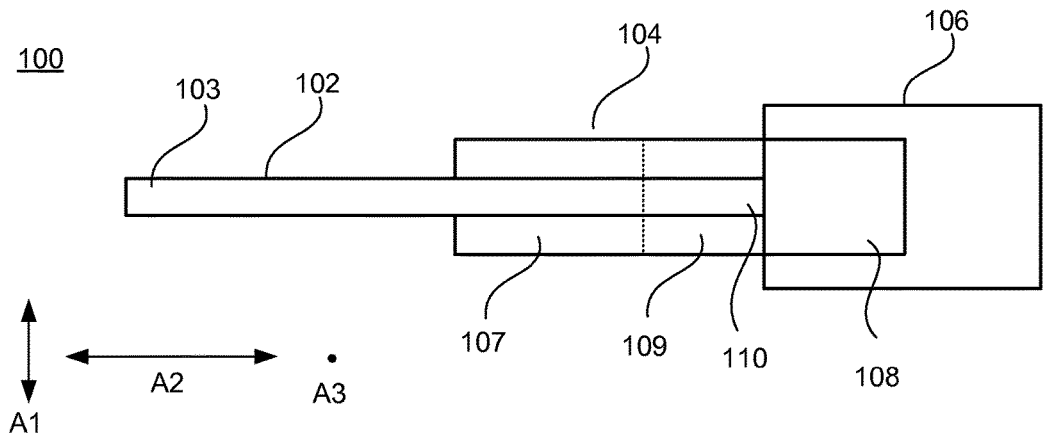
FIG. 1A illustrates a medical device having a pusher member within a first configuration in relation to a handle according to an aspect.
Figure 1B:
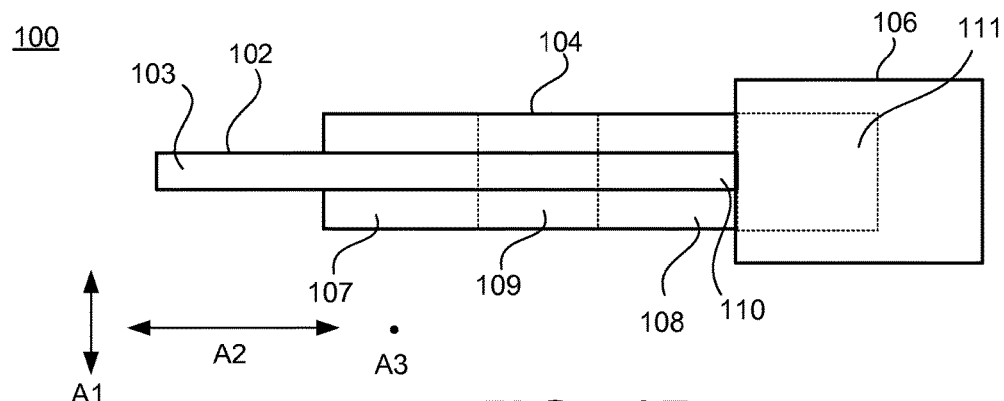
FIG. 1B illustrates the pusher member within a second configuration in relation to handle 106 according to an aspect.
Figure 1C:
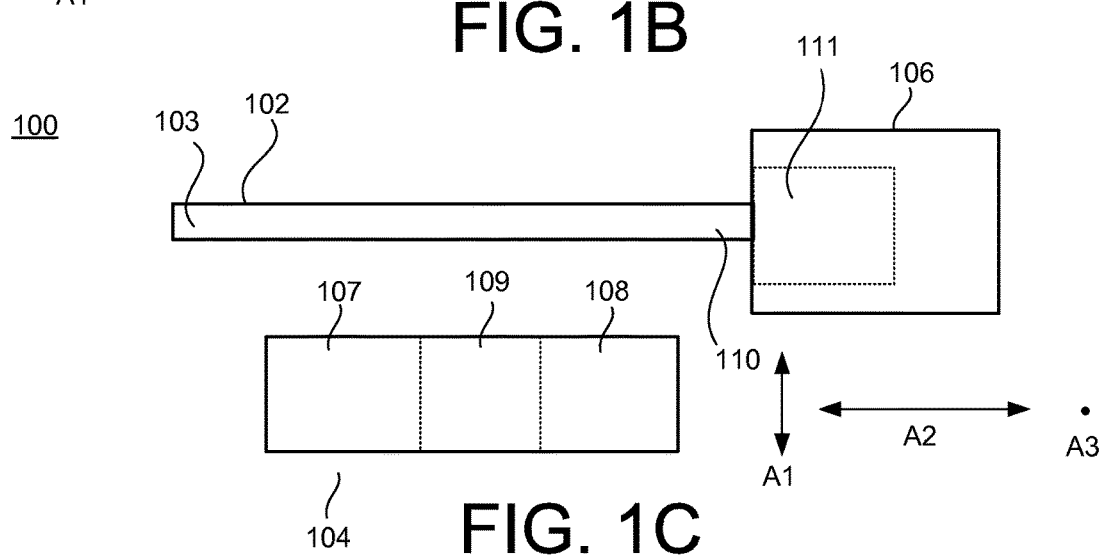
FIG. 1C illustrates the pusher member decoupled from the handle and the needle member according to an aspect.

FIGS. 1A-1C illustrate a medical device 100 having a needle member 102, a handle 106 coupled to the needle member 102, and a pusher member 104 removably coupled to the handle 106 and the needle member 102 according to an aspect. The medical device 100 may be a delivery device for the delivery of implants (e.g., slings, graphs, etc.) into the body of the patient. In some examples, the medical device 100 may be used to delivery mid-urethral slings into the body of the patient.

In some examples, the pusher member 104 may be slidably coupled to the handle 106 such that the pusher member 104 may slide relative to the handle 106 during a surgical procedure. For example, during a surgical procedure, the pusher member 104 may distally slide along a portion of the needle member 102 along an axis A2 to assist with the delivery of the implant or sling. However, after the surgical procedure, the pusher member 104 may be de-coupled from the handle 106 and the needle member 102 so that these components can be sterilized and then re-assembled to be re-used in a subsequent medical procedure. In particular, the pusher member 104 (e.g., the lumen of the pusher member 104) can be removed in order to be cleaned and sterilized since this component is relatively difficult to clean if fixedly coupled to the handle 106 and/or the needle member 102. The axis A2 may be parallel to a longitudinal axis of the medical device 100. An axis A1 may be perpendicular to the axis A2. An axis A3 into the page (shown as a dot) is orthogonal to the axes A1 and A2. The axes A1, A2, and A3 are used throughout several of the various views of the implementations described throughout the figures for simplicity.

Further, the pusher member 104 is removably coupled to the needle member 102 and the handle 106 in a manner that permits the pusher member 104 to slide in relation to the handle 106 in order to assist with the delivery of the implant, but prevents the pusher member 104 from accidentally being de-coupled from the handle 106 and/or the needle member 102 during the surgical procedure. However, after the surgical procedure, the pusher member 104 may be manipulated in order to decouple the pusher member 104 from the handle 106 and the needle member 102. Further, in some examples, the needle member 102 may be decoupled from the handle 106. As such, the medical device 100 may be considered a re-usable medical delivery device since at least some of its components can be disassembled, sterilized, and then re-assembled for future use. In some examples, the medical device 100 may be a reusable mid-urethral sling delivery device.

FIG. 1A illustrates the pusher member 104 within a first configuration (e.g., a retracted position) in relation to the handle 106 according to an aspect. FIG. 1B illustrates the pusher member 104 within a second configuration (e.g., an extended position) in relation to the handle 106 according to an aspect. FIG. 1C illustrates the pusher member 104 decoupled from the handle 106 and the needle member 102.

Referring to FIGS. 1A-1C, the needle member 102 may be an elongated cylindrical structure. The needle member 102 may include one or more curved portions in two or three dimensional planes. In other examples, the needle member 102 may be substantially straight. In other examples, the needle member 102 may include one or more bent portions. The needle member 102 may include portions having different diameters such as a reduced diameter portion. In some examples, the needle member 102 may include portions having a non-cylindrical structure such as a D-shaped structure. The needle member 102 may include a metal or metal-based material such as stainless steel. The needle member 102 may define a lumen. In other examples, the needle member 102 may be solid (e.g., without a lumen).

The needle member 102 may include a distal end portion 103 and a proximal end portion 110. The distal end portion 103 may be configured to pierce or penetrate bodily tissue when inserted into the body. In some examples, the distal end portion 103 may be a sharp tip portion. In other examples, the distal end portion 103 may be a blunt tip portion or a round tip portion. In some examples, the distal end portion 103 may include a coupling member configured to couple an implant to the needle member 102. In particular, the distal end portion 103 may define a slot (e.g., L-shaped slot) configured to couple an implant to the needle member 102.

The proximal end portion 110 of the needle member 102 may be coupled to the handle 106. In some examples, the proximal end portion 110 of the needle member 102 may be fixedly coupled to the handle 106. For example, the proximal end portion 110 of the needle member 102 may be coupled to the handle 106 using an adhesive or bonding material. In some examples, the proximal end portion 110 of the needle member 102 may include a threaded (male or female) portion such that the threaded male portion is inserted into a threaded (male or female) portion of the handle 106, and the threaded portions are secured using an adhesive or bonding material. However, any medical device described herein may encompass any type of coupling mechanism to securely couple the needle member 102 to the proximal end portion 110 of the needle member 102.

In other examples, the proximal end portion 110 of the needle member 102 may be removably coupled to the handle 106 such that the needle member 102 and the handle 106 may be de-coupled, and thereby cleaned separately. In some examples, the proximal end portion 110 may include a threaded male portion such that the threaded male portion is inserted into a threaded female portion of the handle 106. It is noted that any medical device described herein may encompass the reverse situation of using the threaded female portion for the proximal end portion 110 and the threaded male portion for the handle 106. Also, any type of coupling mechanism may be used to removably couple the needle member 102 to the proximal end portion 110 of the needle member 102.

The handle 106 may include a structure configured to be grasped by an operator. In some examples, the handle 106 may be a metal, metal-based, plastic, or plastic-based material. In some examples, the handle 106 may include an opening configured to receive the proximal end portion 110 of the needle member 102. In some examples, the handle 106 may define a secondary opening on the other end of the handle 106. In some examples, the handle 106 may define a lumen that may extend between the openings.

The handle 106 may define a track portion 111. A portion of the pusher member 104 (e.g., extension member 108) may be slidably coupled to the track portion 111. The track portion 111 may be configured to engage with the portion of the pusher member 104 such that the pusher member 104 can slide relative to at least a portion of the track portion 111. Also, the track portion 111 (in conjunction with features on the pusher member 104) may limit the travel distance during the surgical procedure. In some examples, the track portion 111 may allow movement of the pusher member 104, but prevent the pusher member 104 from being accidently decoupled from the handle 106 during the surgical procedure. In some examples, the track portion 111 may define a recess from the top surface of the handle 106. In some examples, the track portion 111 may include projections, extensions, and/or enlarged portions that extend into the recess in order to limit the movement of the pusher member 104. In some examples, the track portion 111 may include features that permit the pusher member 104 to be de-coupled from the handle 106. In some examples, the pusher member 104 may rotate off the track portion 111.

The pusher member 104 may be configured to slide along the axis A2 from the retracted position (e.g., FIG. 1A) to the extended position (e.g., FIG. 1B) (or any position between the retracted position and the extended position) during the surgical procedure. The pusher member 104 can push an anchor or other implant off the needle member 102 during the surgical procedure. Also, the pusher member 104 may be decoupled from the handle 106 and the needle member 102 (e.g., FIG. 1C). The pusher member 104 may include a sheath 107, a handle portion 109, and an extension member 108. In some examples, the handle portion 109 may be disposed between the sheath 107 and the extension member 108. In some examples, the sheath 107, the handle portion 109, and the extension member 108 may define different shapes or structures. In some examples, the sheath 107, the handle portion 109, and/or the extension member 108 may be unitarily formed. In other examples, the sheath 107, the handle portion 109, and/or the extension member 108 may be separately formed and coupled together. Also, the sheath 107, the handle portion 109, and the extension member 108 may be made from the same or similar type of materials or different materials.

The sheath 107 may be configured to be disposed around a portion of the needle member 102. In some examples, the sheath 107 may be a cylindrical structure. Similar to the sheath 107, the handle portion 109 may be configured to be disposed around a portion of the needle member 102. The handle portion 109 may have a structure configured to be grasped by an operator of the medical device 100. For example, an operator may grasp the handle portion 109 of the pusher member 104 and the handle 106 to slide the pusher member 104 during the surgical procedure.

The sheath 107 and the handle portion 109 may define an internal lumen that extends through the length of the sheath 107 and the handle portion 109 (e.g., along the axis A2). The size of the lumen may be larger than the diameter of the needle member 102 such that the needle member 102 can be disposed within the lumen of the sheath 107 and the handle portion 109. In some examples, the sheath 107 and the handle portion 109 may define a slot having a depth such that it extends into the lumen (e.g., along the axis A3) and a length such that it extends along the entire length of the sheath 107 and handle portion 109 along the axis A2. The slot may permit the pusher member 104 to be decoupled from the needle member 102 may moving the pusher member 104 in any direction perpendicular to the axis A1.

The extension member 108 may be configured to proximally extend from the handle portion 109 along the axis A2. The extension member 108 may extend from a top or bottom surface of a proximal end portion of the handle portion 109. The extension member 108 may be slidably coupled to the track portion 111 of the handle 106 such that the extension member 108 may travel a certain limited distance during the surgical procedure. In some examples, the extension member 108 may be slightly flexible such that the extension member 108 may bend. The extension member 108 may have a structure that corresponds to the track portion 111. The extension member 108 may fit within the recess defined by the track portion 111. In some examples, the extension member 108 may define an opening, slot, or cut-out portion that permits the extension member 108 to be de-coupled from the handle 106 by rotation or by applying increased force substantially along the axis A2. In some examples, the extension member 108 may include protrusions, extensions, and/or enlarged portions that engage with the handle 106 to limit the movement of the pusher member 104 during the surgical procedure.

Figure 2A:
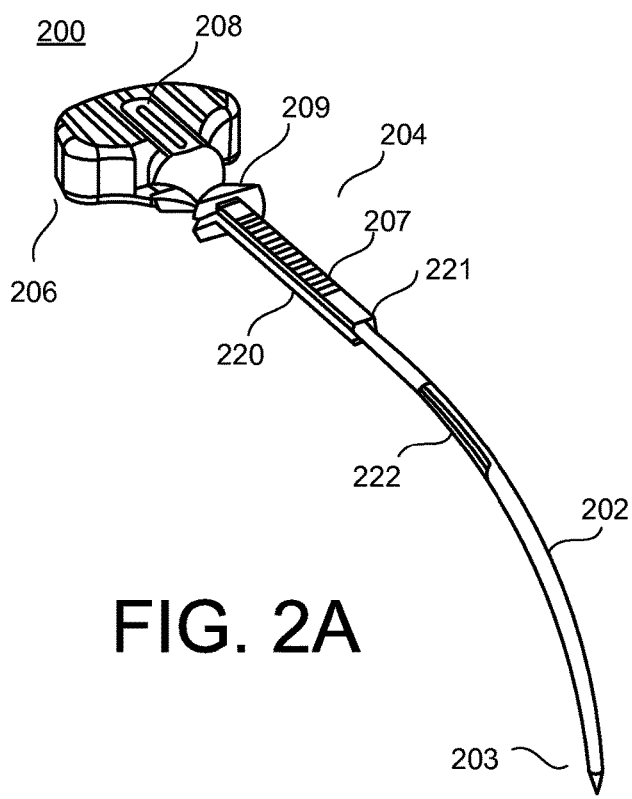
FIG. 2A illustrates a medical device having assembled components according to an aspect.
Figure 2B:
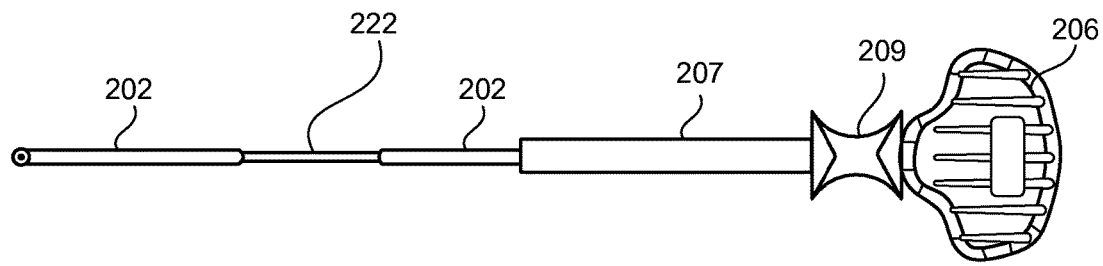
FIG. 2B illustrates a top view of the medical device of FIG. 2A according to an aspect.

FIGS. 2A-2G illustrate components of a medical device 200 that may be disassembled and reassembled according to various aspects. FIG. 2A illustrates a perspective of the medical device 200 having the assembled components. FIG. 2B illustrates a top view of the medical device 200 of FIG. 2A. Referring to FIGS. 2A and 2B, the medical device 200 may include a handle 206, a needle member 202 coupled to the handle 206, and a pusher member 204 having an extension member 208, a handle portion 209, and a sheath 207. The pusher member 204 may be configured to slide along the needle member 202 for a distance corresponding to a length of at least a portion of the extension member 208 during the surgical procedure.

Figure 2C:
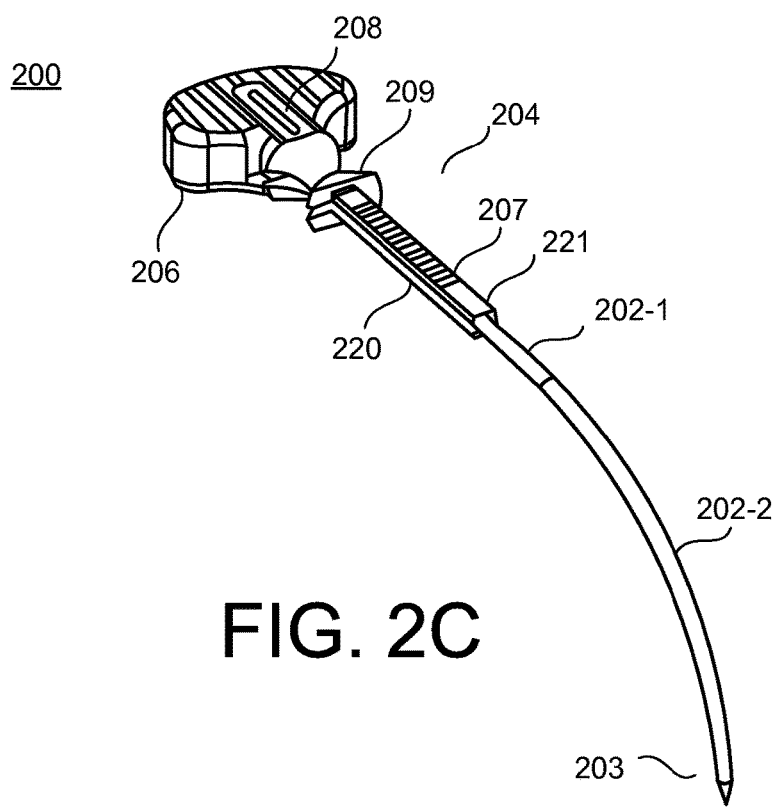
FIG. 2C illustrates the medical device of FIG. 2A according to another aspect.

Also, referring to FIGS. 2A-2B, the needle member 202 may include a reduced diameter portion 222. However, the needle member 202 is not required or need to have any additional reduced diameter portions. As such, in some examples, the needle member 202 does not include the reduced diameter portion 222. In some examples, the reduced diameter portion 222 may assist in allowing the pusher member 204 to slide off the needle member 202. This feature is further explained with reference to FIGS. 5A-5E. The reduced diameter portion 222 may be a section of the needle member 202 between a proximal end portion 221 of the pusher member 204 and a distal end portion 203 of the needle member 202. The needle member 202 may have a first diameter. The reduced diameter portion 222 may have a second diameter. The second diameter may be less than the first diameter. Turning to FIG. 2C, instead of using the reduced diameter portion 222, the needle member 202 may include a first needle member portion 202-1 having a first diameter, and a second needle member portion 202-2 having a second diameter. In this example, the second needle member portion 202-2 may extend to the distal end portion 203 of the needle member 202. The second diameter may be less than the first diameter. The second needle member portion 202-2 may assist in allowing the pusher member 204 to slide off the needle member 202. Again, the needle member 202 does not need any reduced diameter portions or sections to facilitate the removal of the pusher member 204. As such, in other examples, the needle member 202 does not include a reduced diameter portion 222 or a section 202 having a reduced diameter.

Referring to FIG. 2A, the needle member 202 may include a distal end portion 203. The distal end portion 203 may be tapered. The distal end portion 203 may include a sharp tip portion. In other examples, the distal end portion 203 may include a blunt or rounded tip portion. The proximal end portion of the needle member 202 may be coupled to the handle 206. Also, the needle member 202 may include one or more curved portions, bent portions, and/or other non-cylindrical portions.

The pusher member 204 may define a lumen extending through the handle portion 209 and the sheath 207 such that the needle member 202 can extend through the handle portion 209 and the sheath 207. Also, as shown in FIG. 2A, the pusher member 204 may define a slot 220. For example, the slot 220 may extend through or along the length of the handle portion 209 and the sheath 207. As such, the structure of the pusher member 204 defining the lumen and the slot 220 may be substantially c-shaped or u-shaped. In some examples, when the pusher member 204 is coupled to the handle 206, the slot 220 may be disposed on a side portion of the pusher member 204. In the retracted position (e.g., FIG. 2A), the extension member 208 may be configured to overlap with a portion of a top surface of the handle 106. The details of the handle 206 are further described with respect to FIGS. 2D and 2E, and the details of the pusher member 204 are further described with respect to FIGS. 2F and 2G.

Figures 2D, 2E:
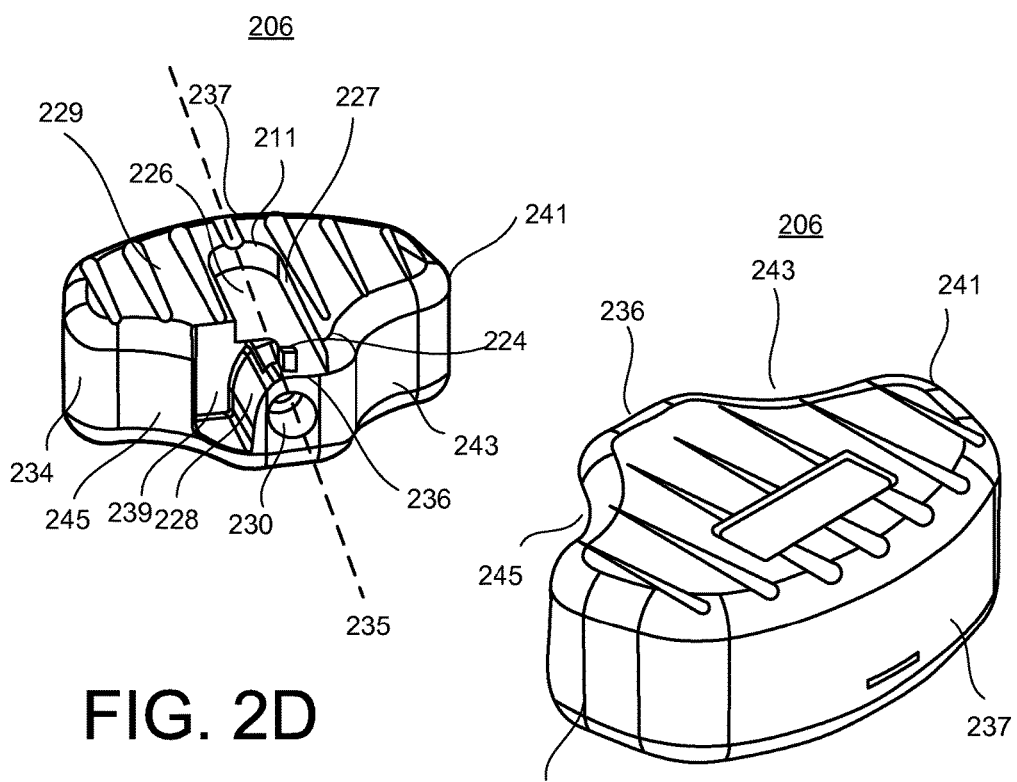
FIG. 2D illustrate a top perspective of the handle according to an aspect.
FIG. 2E illustrates a bottom perspective of the handle according to an aspect.

FIGS. 2D and 2E illustrate a more detailed view of the handle 206. FIG. 2D illustrates a top perspective of the handle 206. FIG. 2E illustrates a bottom perspective of the handle 206.

Referring to FIGS. 2E and 2D, the handle 206 may have a proximal end portion 237, a distal end portion 236, a first side portion 234, and a second side portion 241. Also, the handle 206 may have a first concave portion 245 between the distal end portion 236 and the first side portion 234, and a second concave portion 243 between the distal end portion 236 and the second side portion 241.

Referring to FIG. 2D, the handle 206 may define a track portion 211. The track portion 211 may include a recess 226. In some examples, the recess 226 may have a shape that corresponds to the extension member 208 of the pusher member 204 such that the extension member 208 can fit and slide within the recess 226. In some examples, the recess 226 may have a u-shape structure such that lateral edges 227 that define the u-shaped recess are disposed parallel with the longitudinal axis 235 of the handle 206, and the rounded portion of the u-shaped recess intersects with the longitudinal axis 235 of the handle 206. Portions of the recess 226 extend on both sides the longitudinal axis 235 of the handle 206. The recess 226 may extend below a top surface 229 of the handle 206. The recess 226 may have a length extending from start of the recess (e.g., the distal end portion 236 of the handle 206 to the end of the recess (e.g., a location proximate to the proximal end portion 237 of the handle 206).

The track portion 211 may include a protrusion 224. The protrusion 224 may be configured to prevent the pusher member 204 from being de-coupled from the handle 206 during a surgical procedure. This feature is further explained with reference to FIGS. 2F and 2G. The track portion 211 may define a travel distance of the pusher member 204. In particular, the travel distance may be defined by the length of the recess 226 from the protrusion 224 to the end of the recess 226. As such, the protrusion 224 prevents the pusher member 204 from being accidentally released from the handle 206 during the surgical procedure.

Figure 2F:
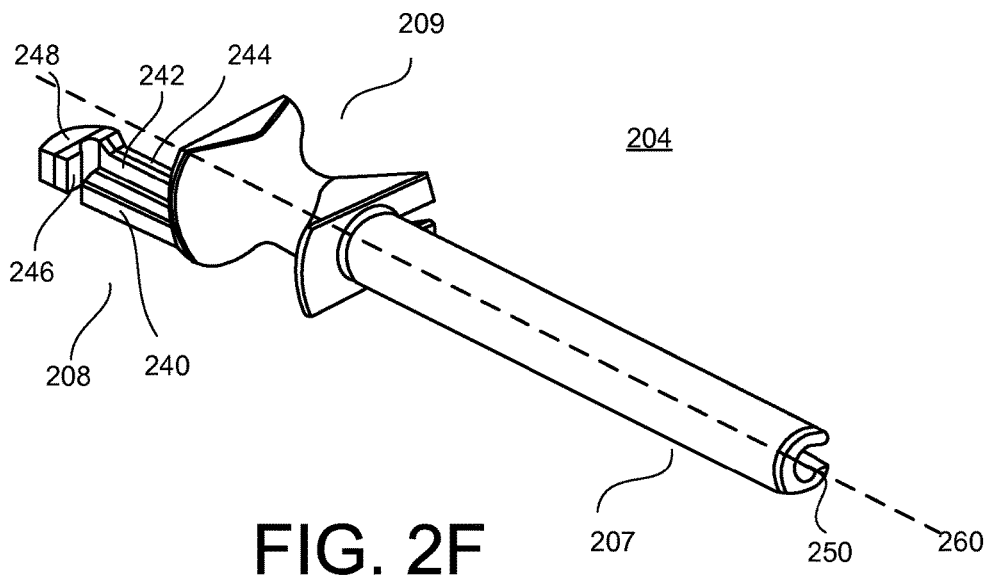
FIG. 2F illustrates a first side perspective of the pusher member according to an aspect.

The handle 206 may define a cut-out portion 239 and a recessed side portion 228. When the pusher member 204 is in the extended position (e.g., close to or engaging the protrusion 224), the cut-out portion 239 and the recessed side portion 228 permit the pusher member 204 to rotate with respect to the handle 206, thereby de-coupling the pusher member 204 from the handle 206. For example, the slot 246 of the extension member 208 (e.g., the slot 246 is shown in FIG. 2F) may be configured to slide past the protrusion 224 when the pusher member 204 is rotated. The recessed side portion 228 may be proximate to the recess 226. The recessed side portion 228 may include a curved portion or a slope portion. The recessed side portion 228 may be recessed from the first concave portion 245. Also, the handle 206 may define an opening 230 that extends into the body of the handle 206. The opening 230 may be the opening to the lumen extending into the handle 206. The size of the opening 230 may be slightly larger than a diameter of the needle member 202 such that the needle member 202 can fit within the opening 230.

Figure 2G:
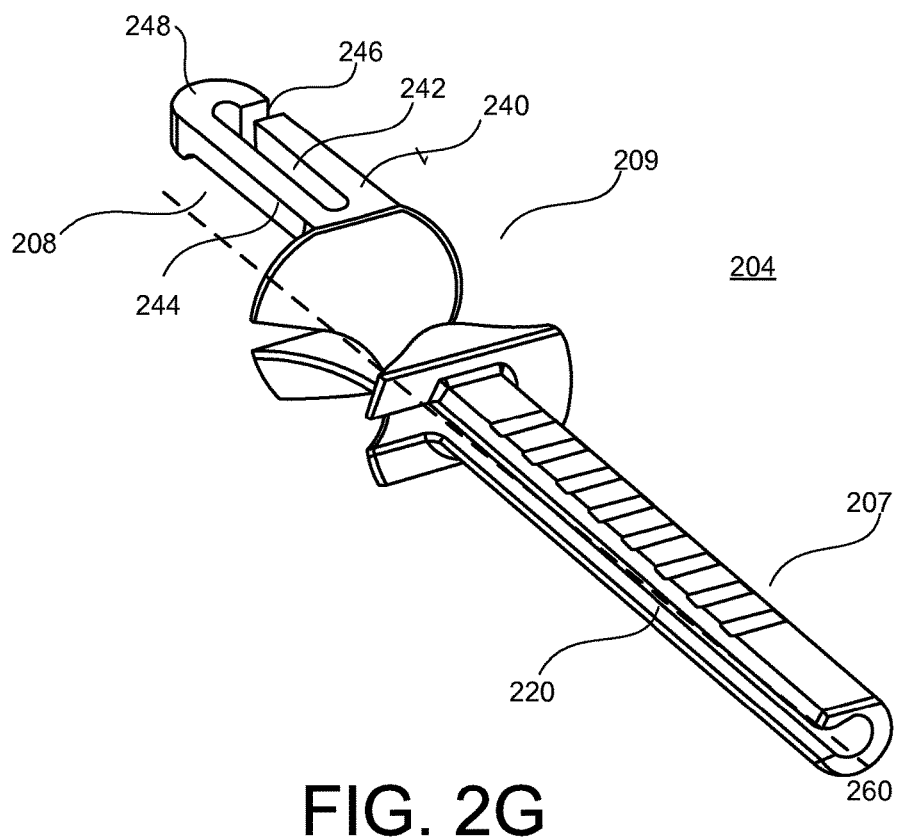
FIG. 2G illustrates a second side perspective of the pusher member according to an aspect.

FIGS. 2F and 2G illustrate a more detailed view of the pusher member 204. FIG. 2F illustrate a first side view of the pusher member 204. FIG. 2G illustrates a second side view of the pusher member 204. As shown in FIGS. 2F and 2G, the pusher member 204 may include the extension member 208, the handle portion 209, and the sheath 207. The pusher member 204 may define a longitudinal axis 260.

The sheath 207 may include a cylindrical structure defining (in part) the slot 220. The slot 220 permits the pusher member 204 to be released from the needle member 202 from the side. The cylindrical structure of the sheath 207 may define (in part) a lumen 250. The longitudinal axis 260 may be defined by a center axis of the lumen 250. Portions of the needle member 202 may be disposed within the lumen 250. In some examples, the cylindrical structure may be u-shaped. The handle portion 209 may also define the lumen 250 and the slot 220 such that the lumen 250 and the slot 220 extend through the length of the handle portion 209 and the sheath 207. The handle portion 209 may define a structure configured to be grasped by an operator of the medical device 200.

The extension member 208 may extend from a proximal end portion of the handle portion 209. In some examples, the extension member 208 may extend from a top surface of the handle portion 209. The extension member 208 may extend in a direction parallel with the longitudinal axis 260. In some examples, the extension member 208 may define an opening 242 within a perimeter of the extension member 208 (e.g., the structure of the extension member 208 may have a perimeter portion defining an inner perimeter and an outer perimeter). Also, the extension member 208 may define a slot 246. The extension member 208 may include a first side portion 244, a second side portion 240, and a connector portion 248 that connects the first side portion 244 with the second side portion 240. In some examples, the first side portion 244 may define the slot 246. In other examples, the second side portion 240 may define the slot 246.

Figure 3A:
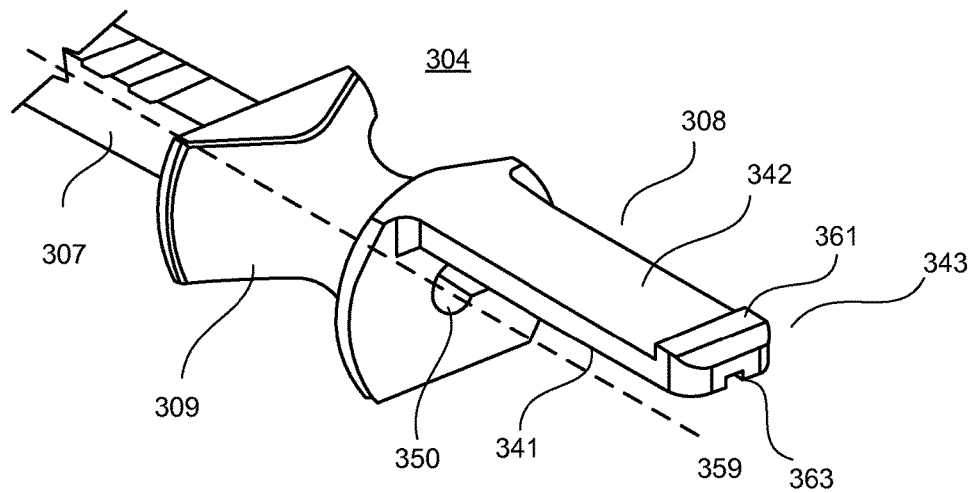
FIG. 3A illustrates a pusher member according to another aspect.
Figure 3B:
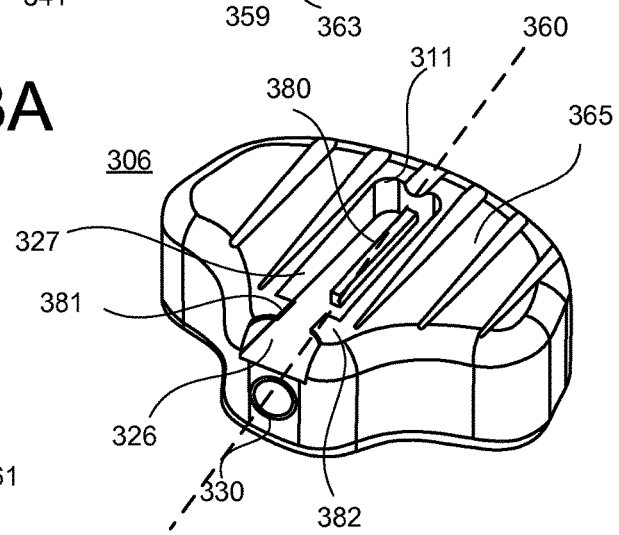
FIG. 3B illustrates a handle according to another aspect.
Figure 3C:
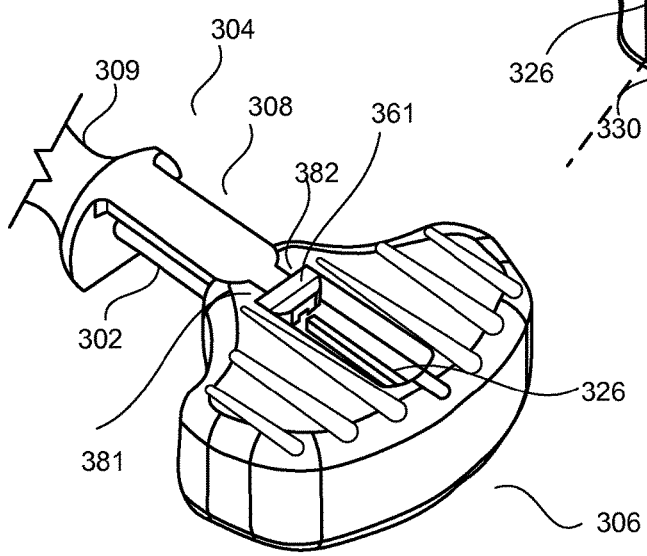
FIG. 3C illustrates the pusher member and the handle of FIGS. 3A and 3B according to an aspect.
Figure 3D:
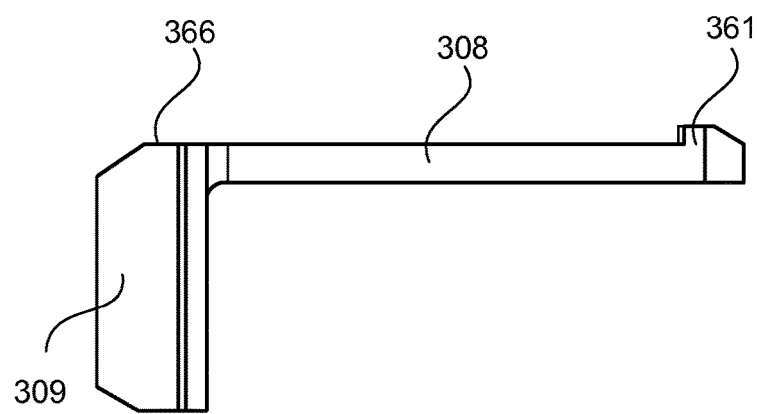
FIG. 3D illustrates a side view of the pusher member according to an aspect.

FIGS. 3A-3D illustrates a pusher member 304 and a handle 306 according to various aspects. FIG. 3A illustrates a perspective of the pusher member 304 having a sheath 307, a handle portion 309, and an extension member 308. The sheath 307 and the handle portion 309 may be the same as the sheath 207 and the handle portion 209 described with reference to FIGS. 2A-2G, and therefore the details of these components will be omitted for the sake of brevity. FIG. 3B illustrates a perspective of the handle 306. FIG. 3C illustrates the pusher member 304 coupled to the handle 306 with a needle member 302 coupled to the handle 306 and extending through the pusher member 304. FIG. 3D illustrates a side view of the extension member 308 of the pusher member 304 and a portion of the handle portion 309.

In the aspects of FIGS. 3A-3D, the extension member 308 of the pusher member 304 may include a lip 361 and a groove 363, and the handle 306 may include protrusions 381, 382 configured to engage the lip 361 and a guider 380 configured to be disposed within the groove 363. The guider 380 may guide the extension member 308 as the pusher member 304 slides in relation to the handle 306.

Referring to FIG. 3A, the extension member 308 may extend from a proximal end portion of the handle portion 309. Referring to FIG. 3D, the extension member 308 may extend from a top surface 366 of the proximal end portion of the handle portion 309. Referring back to FIG. 3A, the extension member 308 may extend in a direction parallel with a longitudinal axis 359 of the pusher member 304. In some examples, the extension member 308 may be substantially rectangular. In some examples, the extension member 308 does not have any openings or through-holes extending through a thickness of the extension member 308. The extension member 308 may include a top surface 342 and a bottom surface 341. The bottom surface 341 of the extension member 308 may define the groove 363. The groove 363 may be disposed in the middle portion of the extension member 308 and extend in a direction parallel to the longitudinal axis 359 of the pusher member 304. The proximal end portion 343 of the extension member 308 may include the lip 361. The lip 361 may extend above the top surface 342 of the extension member 308. Also, the proximal end portion 343 of the extension member 308 may include curved or rounded portions along portions of the sides of the proximal end portion 343.

Referring to FIG. 3B, the handle 306 may include a track portion 311. The track portion 311 may define a recess 326 having the guider 380, a first protrusion 381 and a second protrusion 382, and an opening 330 configured to receive the needle member 302. The recess 326 may have a shape that substantially corresponds to the shape of the extension member 308 such that the extension member 308 can fit and slide within the recess 326. In some examples, the recess 326 may have a u-shape structure such that lateral edges 327 are disposed parallel with a longitudinal axis 360 of the handle 306, and the rounded portion of the u-shaped recess intersects with the longitudinal axis 360 of the handle 306. In some examples, the recess 326 may be disposed below the top surface 365 of the handle 306.

The guider 380 may be disposed on a surface of the recess 326. The guider 380 may extend in a direction parallel to the longitudinal axis 360 of the handle 306. The guider 380 may have a length shorter than the length of the recess. The first protrusion 381 may extend from the top surface 365 on one side of the recess 326, and the second protrusion 382 may extend from the top surface 365 on the other side of the recess 326. The first protrusion 381 and the second protrusion 382 may be disposed towards the start (e.g., distal end) of the recess 326. In some examples, the first protrusion 381 and the second protrusion 382 may be offset from the start of the recess 326. The first protrusion 381 and the second protrusion 382 may slide over the top surface 342 of the extension member 308.

Referring to FIG. 3C, the extension member 308 may be configured to slide in relation to the handle 306. For example, the extension member 308 may be disposed within the recess 326 such that the first protrusion 381 and the second protrusion 382 are disposed over the top surface 342 of the extension member 308. Also, the guider 380 may be slidably disposed within the groove 363. The extension member 308 may be configured to travel the distance between the protrusions 381, 382 and the back edge of the recess 326. In the retracted position, the proximal end portion 343 of the extension member 308 may engage the back edge of the recess 326. In the extended position (as shown in FIG. 3C), the lip 361 may engage the protrusions 381, 382, thereby limiting the distance. In order to remove the pusher member 304 from the handle 306, the lip 361 may be pushed down such that the proximal end portion 343 bends towards the surface of the recess 326. Then, the lip 361 may slide underneath the protrusions 381, 382, thereby de-coupling the pusher member 304 from the handle 306. Then, the pusher member 304 may be distally moved along the needle member 302, and the pusher member 304 may be removed from the needle member 302 through the slot defined by the pusher member 304.

FIGS. 4A-4C illustrates a pusher member 404 and a handle 406 according to various aspects. FIG. 4A illustrates a perspective of the pusher member 404 having a sheath 407, a handle portion 409, and an extension member 408. The sheath 407 and the handle portion 409 may be the same as the sheath 207 and the handle portion 209 described with reference to FIGS. 2A-2G, and therefore the details of these components will be omitted for the sake of brevity. FIG. 4B illustrates a perspective of the handle 406. FIG. 4C illustrates the pusher member 404 coupled to the handle 406 with a needle member 402 coupled to the handle 406 and extending through the pusher member 404.

In the aspects of FIGS. 4A-4C, the extension member 408 of the pusher member 404 may define a prong having two extensions 470, 471 with enlarged portions 472, 473, and the handle 406 may include tapered portions 475, 476 configured to engage the enlarged portions 472, 473 to limit a travel distance of the pusher member 404 during the surgical procedure. The pusher member 404 may be removed the handle 406 may applying additional force in the distal direction such that the enlarged portions 472, 473 are moved closer together to fit past the tapered portions 475, 476.

Referring to FIG. 4A, the extension member 408 may extend from the end of the handle portion 409. The extension member 408 may extend in a direction parallel with a longitudinal axis 459 of the pusher member 404. The extension member 408 may define a prong having a first extension member 470 and a second extension member 471. The first extension member 470 may be parallel with the second extension member 471. The first extension member 470 may be spaced part from the second member extension 471, thereby creating an opening 474 between the first extension member 470 and the second extension member 471. The proximal end portion of the first extension member 470 may include a first enlarged portion 472. The proximal end portion of the second extension member 471 may include a second enlarged portion 473. The first enlarged portion 472 may be aligned with the second enlarged portion 473 in relation to the location along the length of the extension member 408. The first enlarged portion 472 may have a width greater than other portions of the first extension member 470. The second enlarged portion 473 may have a width greater than other portions of the second enlarged portion 473. The width of the first enlarged portion 472 may be the same as the width of the second enlarged portion 473. The opening 474 between the first enlarged portion 472 and the second enlarged portion 473 may be smaller than the opening 474 between the non-enlarged portions of the first extension member 470 and the non-enlarged portions of the second extension member 471.

Referring to FIG. 4B, the handle 406 may include a track portion 411 that couples the extension member 408, and an opening 430 configured to receive the needle member 402. The track portion 411 may include a recess 426, a first tapered portion 475, and a second tapered portion 476. Similar to the handle 306 of FIG. 3B, the recess 426 may have a shape that substantially corresponds to the shape of the extension member 408 such that the extension member 408 can fit and slide within the recess 426.

The first tapered portion 475 may be a portion of the handle 406 that extends into the recess 426 on a first side of the recess 426. The second tapered portion 476 may be a portion of the handle 406 that extends into the recess 426 on a second side of the recess. The first tapered portion 475 and the second tapered portion 476 may be aligned in the same location with respect to the length of the recess. The first tapered portion 475 and the second tapered portion 476 may be disposed on the distal end portion of the handle 406. The width of the recess 426 at the location of the tapered portions 475, 476 may be smaller the width of other portions of the recess 426.

Referring to FIG. 4C, the extension member 408 may be configured to slide in relation to the handle 406. For example, the extension member 408 may be disposed within the recess 426, and the extension member 408 may be configured to travel the distance between the tapered portions 475, 476 and the back edge of the recess 426. In the retracted position, the tapered portions 475, 476 may engage the back edge of the recess 426. In the extended position (as shown in FIG. 4C), the enlarged portions 472, 473 may engage the tapered portions 475, 476, thereby limiting the distance during a surgical procedure. The pusher member 404 may be removed the handle 406 may applying additional force in the distal direction such that the enlarged portions 472, 473 are moved closer together (thereby decreasing the opening 474) in order to fit past the tapered portions 475, 476.

Figure 5A:
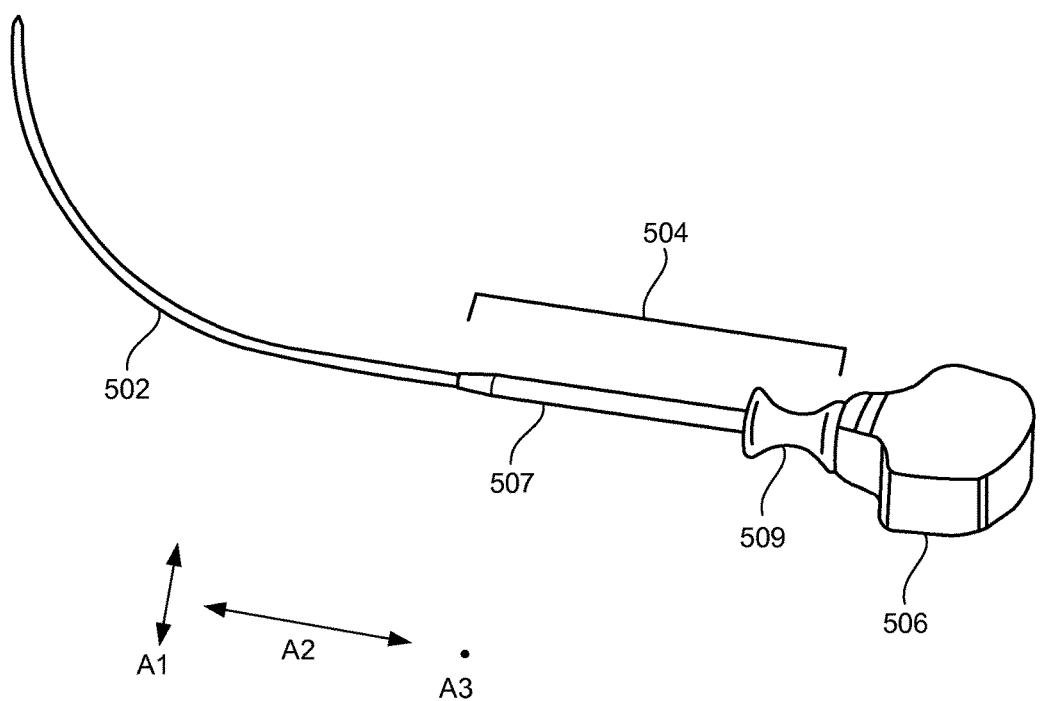
FIG. 5A illustrates a medical device in a first configuration according to an aspect.
Figure 5B:
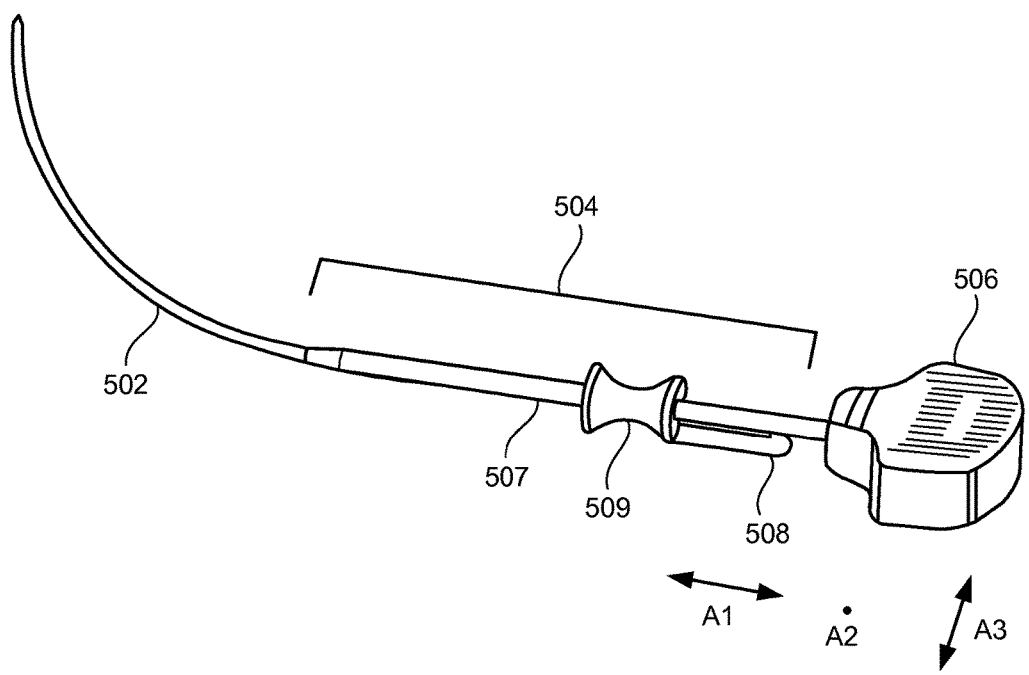
FIG. 5B illustrates a medical device in a second configuration according to an aspect.
Figure 5C:
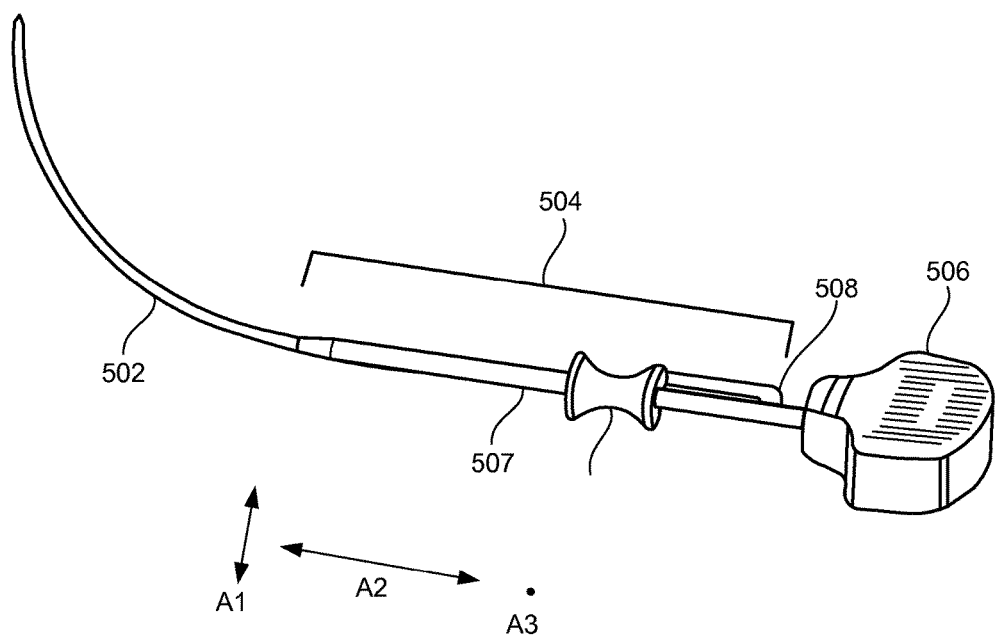
FIG. 5C illustrates a medical device in a third configuration according to an aspect.
Figure 5D:
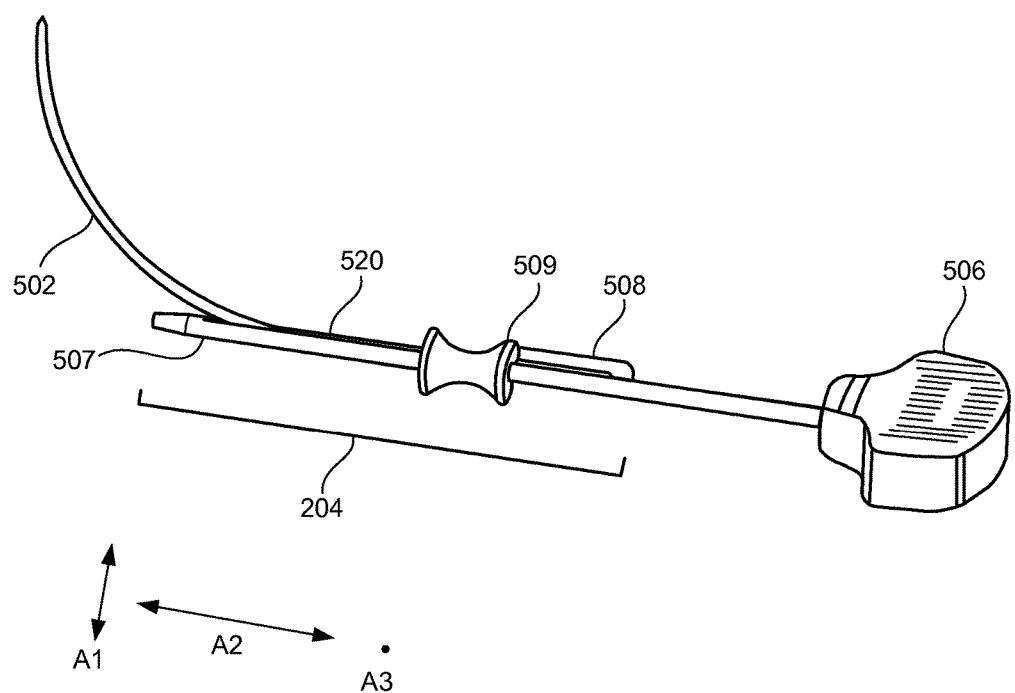
FIG. 5D illustrates a medical device in a fourth configuration according to an aspect.
Figure 5E:
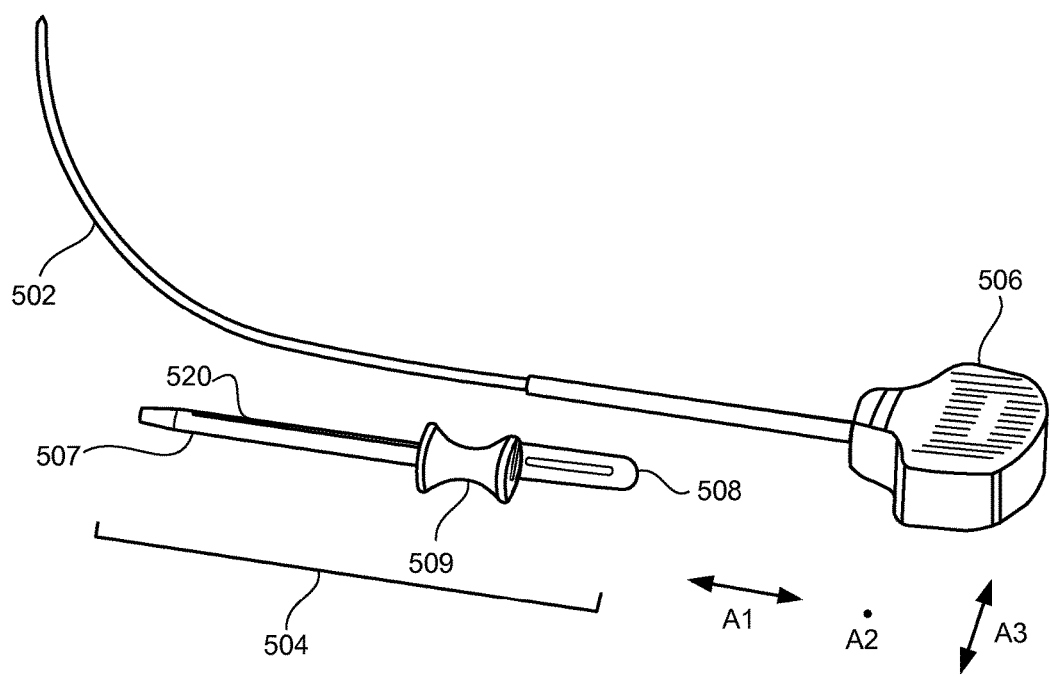
FIG. 5E illustrates a medical device in a fifth configuration according to an aspect.

FIGS. 5A-5E illustrate various positions of a pusher member 504 in relation to a handle 506 and a needle member 502 in order to decouple the pusher member 504 from the handle 506 and the needle member 502 according to various aspects. FIG. 5A illustrates the pusher member 504 in a first position. FIG. 5B illustrates the pusher member 504 in a second position. FIG. 5C illustrates the pusher member 504 in a fourth position. FIG. 5D illustrates the pusher member 504 in a fifth position. FIG. 5E illustrates the pusher member 504 in a sixth position.

Referring to FIG. 5A, the pusher member 504 is within the retracted position. The pusher member 504 may include a sheath 507, a handle portion 509, and an extension member 508 (see FIGS. 5B-E). As indicated above, the sheath 507 and the handle portion 509 may define a lumen. The needle member 502 extends through the lumen of the sheath 507 and the handle portion 509, and the needle member 502 is coupled to the handle 506. Also, the sheath 507 and the handle portion 509 define a slot 520 (see FIG. 5D-5E) that extends the length of the sheath 507 and the handle portion 509.

Referring to FIG. 5B, the pusher member 504 is distally moved away from the handle 506 along the axis A2. In this example, the pusher member 504 has already been de-coupled from the handle 506. For example, the pusher member 504 may been de-coupled in any of the manners previously described with reference to FIGS. 1-4. As such, after the pusher member 504 is de-coupled from the handle 506, the pusher member 504 may be moved a further distance to the position as shown in FIG. 5B. For example, a relatively small distance may exist between the extension member 508 and the handle 506. Also, the extension member 508 may be still aligned with the track portion of the handle 506.

Referring to FIG. 5C, the pusher member 504 may be rotated about the needle member 502. For example, the pusher member 504 may be rotated clockwise or counter clockwise. In some examples, the pusher member 504 may be rotated until the slot 520 is aligned with a curved portion of the needle member 502.

Referring to FIG. 5D, the pusher member 504 is further moved along the needle member 502 along the axis A2. In some examples, the pusher member 504 is moved to a position where a portion of the pusher member 504 is not disposed around the needle member 502. In some examples, the pusher member 504 is moved to a reduced-diameter portion (e.g., as discussed in FIGS. 2A-2C) such that at least a portion of the sheath 507 and/or the handle portion 509 aligns with the reduced-diameter portion of the needle member 502. Referring to FIG. 5E, the pusher member 504 is removed from the needle member 502 by sliding the pusher member 504 in any directions perpendicular to the axis 2 (e.g., along the axis A3) such that pusher member 504 slides off the needle member 502 through the slot 520.

FIGS. 6A-6D illustrate various examples of a medical device 600 having a needle member 602, a pusher member 604, and a handle 606 that can be disassembled and reassembled according to various aspects.

Figure 6A:
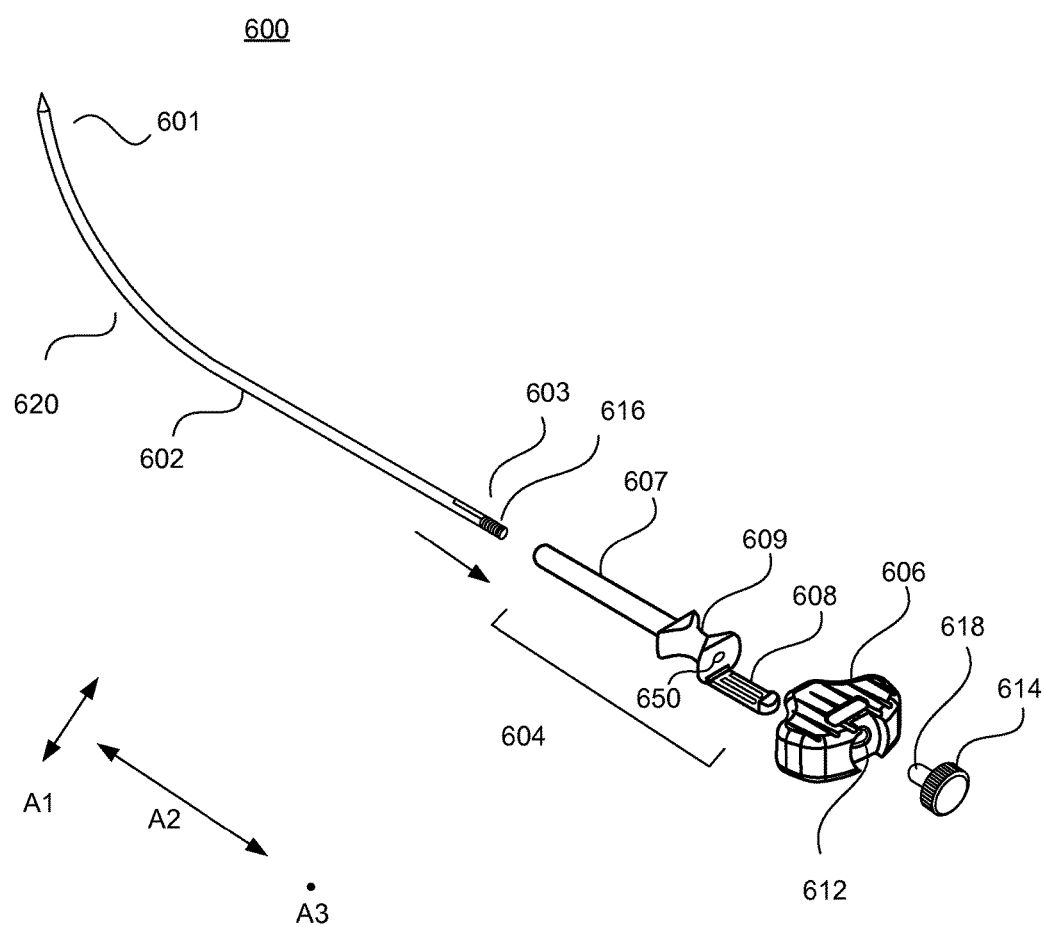
FIG. 6A illustrates a medical device including a needle member, pusher member, and handle in an unassembled configuration according to another aspect.

Referring to FIG. 6A, the needle member 602 may include a curved portion 620. In some examples, the needle member 602 may include multiple curved portions such that the curved portions extend in two or three dimension planes. In other examples, the needle member 602 may be substantially straight. The needle member 602 may include a cylindrical structure. In other examples, the needle member 602 may include portions having a non-cylindrical shape. In some examples, the non-cylindrical shape may be a d-shaped structure having a rounded side and a flat side. The d-shaped structure of the needle member 602 in conjunction with a d-shaped opening on the handle 606 may allow the curved portion 620 of the needle member 602 to be properly orientated, as further described below.

Also, the needle member 602 may include a distal end portion 601 and a proximal end portion 603. The distal end portion 601 may be configured to pierce bodily tissue. In some examples, the distal end portion 601 may be sharp. In some examples, the distal end portion 601 may be blunt or rounded. In some examples, the distal end portion 601 may include a coupling member (e.g., slot) that is configured to couple an implant to the needle member 602. The proximal end portion 603 of the needle member 602 may be coupled to a securing member 614. In some examples, the securing member 614 may be a knob. However, generally, the securing member 614 may be any type of structure configured to be coupled to the proximal end portion 603 of the needle member 602. In some examples, as shown in FIG. 6A, the proximal end portion 603 may include a male thread 616 to be coupled with a female thread 618 of the securing member 614 in order to couple the needle member 602 to the handle 606. In other examples, the proximal end portion 603 may include the female thread 618, and the securing member 614 may include the male thread 616. However, the proximal end portion 603 and the securing member 614 may include any type of fastener/keyway arrangements.

As shown in FIG. 6A, the pusher member 604 may include a sheath 607, a handle portion 609, and an extension member 608. The sheath 607 and the handle portion 609 may define a lumen such that the needle member 602 can extend through the sheath 607 and the handle portion 609. The sheath 607 may be any of the sheaths described with reference to the previous figures, and the handle portion 609 may be any of the handle portions described with reference to the previous figures. However, in some examples, the sheath 607 and the handle portion 609 do not define a slot (e.g., slot 220). In other examples, the sheath 607 and the handle portion 609 include the slot. The extension member 608 may be any of the extension members described with reference to the previous figures.

The handle 606 may be any of the handles described with reference to the previous figures. However, the handle 606 also may include a lumen 612 that extends a length of the handle 606. As shown in FIG. 6A, the proximal end portion 603 may be inserted through the lumen 650 of the sheath 607 and the handle portion 609. The proximal end portion 603 may be further inserted within the lumen 612 of the handle 606. Then, a portion of the securing member 614 may be inserted into the lumen 612 from the other side of the handle 606. The securing member 614 may be manipulated to couple the needle member 602 to the handle 606. In some examples, the male thread 616 of the proximal end portion 603 may engage the female thread 618 of the securing member 614, and the securing member 614 may be rotated, thereby coupling the handle 606 to the needle member 602.

Figure 6B:
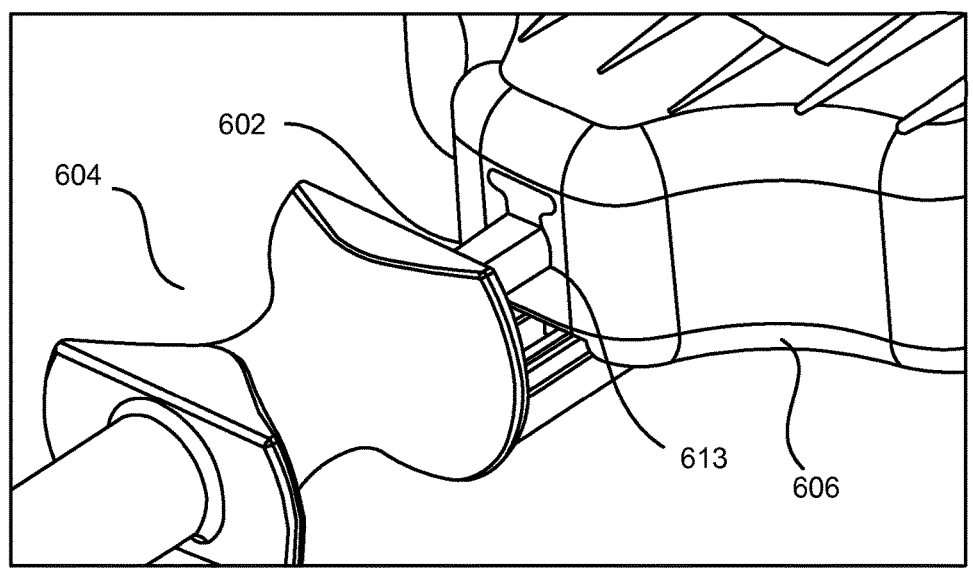
FIG. 6B illustrates a more detailed view of the connection between the handle, the pusher member, and the needle member of FIG. 6A according to an aspect.

FIG. 6B illustrates an opening 613 on the handle 606 according to an aspect. The opening 613 may be configured to receive the proximal end portion 603 of the needle member 602 after it is inserted through the pusher member 604. In some examples, as shown in FIG. 6B, the needle member 602 may have portions that are non-cylindrical. Then, the shape of the opening 613 may be configured to correspond to the shape of the needle member 602. In this manner, the correct orientation of the needle member 602 relative to the handle 606 may be ensured. In some examples, the needle member 602 may be d-shaped having a flat side. In this example, the opening 613 may also be d-shaped in order to position the needle member 602 in a certain orientation.

Figure 6C:
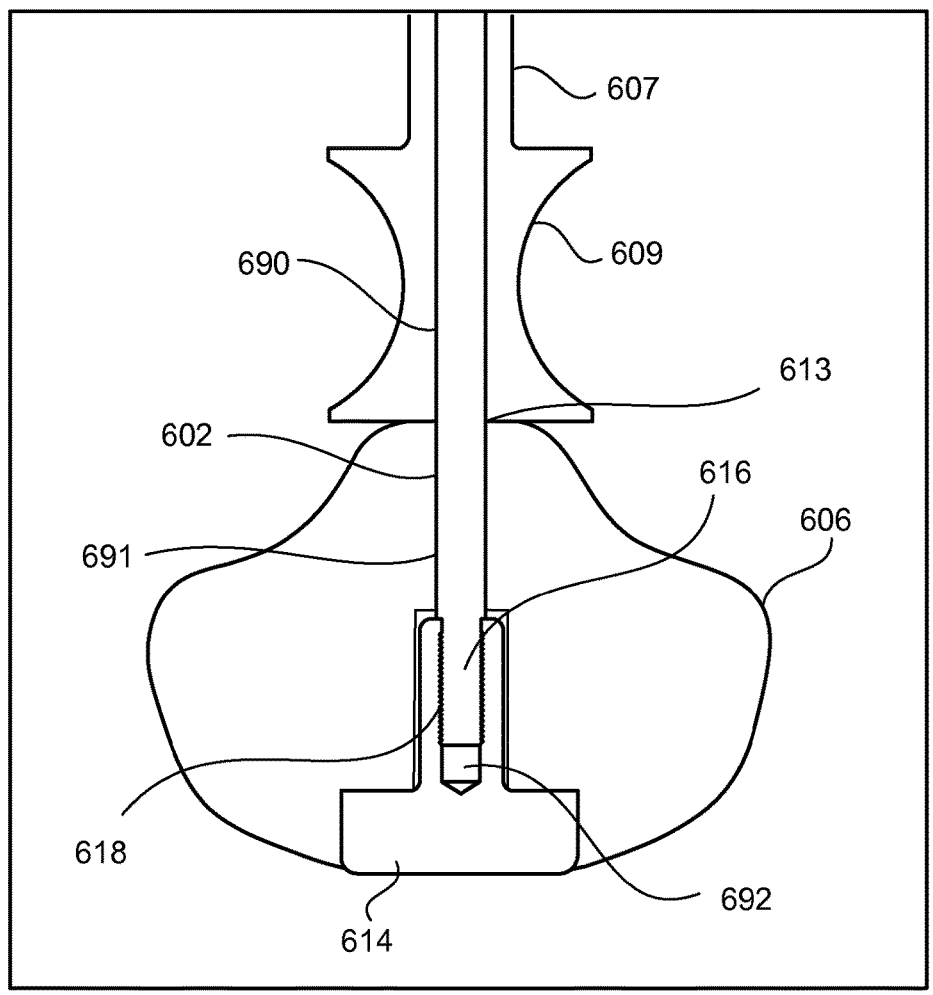
FIG. 6C illustrates a cross-section of the handle, the pusher member, and the needle member of FIG. 6A according to an aspect.

FIG. 6C illustrates a cross-section view depicting the needle member 602 secured to the handle 606 using the securing member 614. As shown, in FIG. 6C, the proximal end portion 603 of the needle member 602 includes the male thread 616. The securing member 614 includes the female thread 618. In the locked configuration as shown in FIG. 6C, a first portion 690 of the needle member 602 extends from the opening 613 through the handle portion 609 and the sheath 607, and a second portion 691 of the needle member 602 is disposed within the handle 606. The second portion 691 includes the male thread 616 and a portion 692 that extends beyond the male thread 616. As shown in FIG. 6C, the needle member 602 does not extend through the length of the handle 606. In some examples, the securing member 614 may be disposed entirely within the handle 606. In other examples, the securing member 614 may be partially disposed within the handle 606.

Figure 6D:
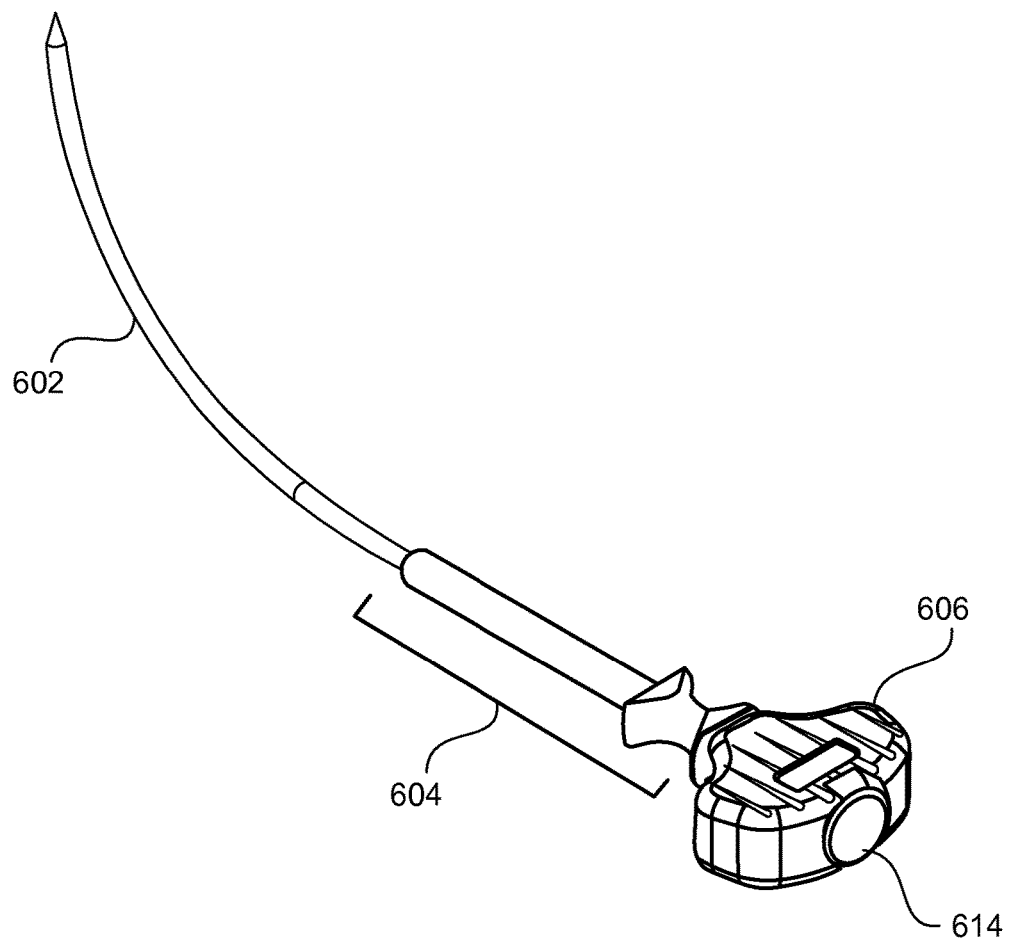
FIG. 6D illustrates the medical device of FIG. 6A in an assembled configuration according to an aspect.

FIG. 6D illustrates the medical device 600 as assembled according to an aspect. As shown in FIG. 6D, the needle member 602 is coupled to the handle 606 using the securing member 614, and the needle member 602 is disposed within a lumen defined by the pusher member 604 such that the pusher member 604 can move relative to the handle 606.

Figure 7A:
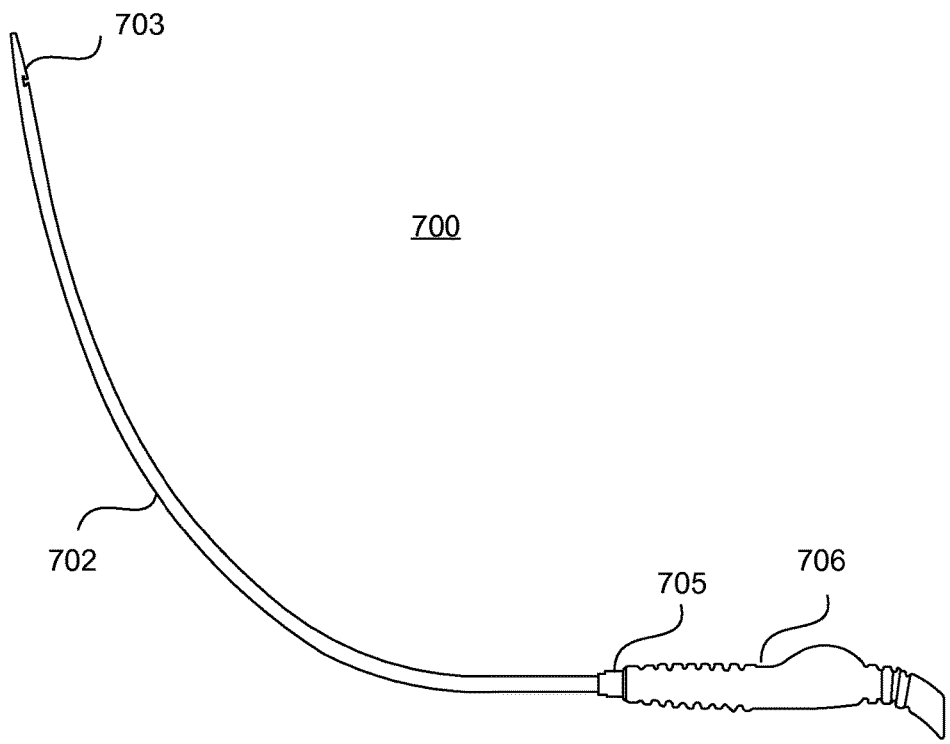
FIG. 7A illustrates a side view of a medical device according to another aspect.
Figure 7B:
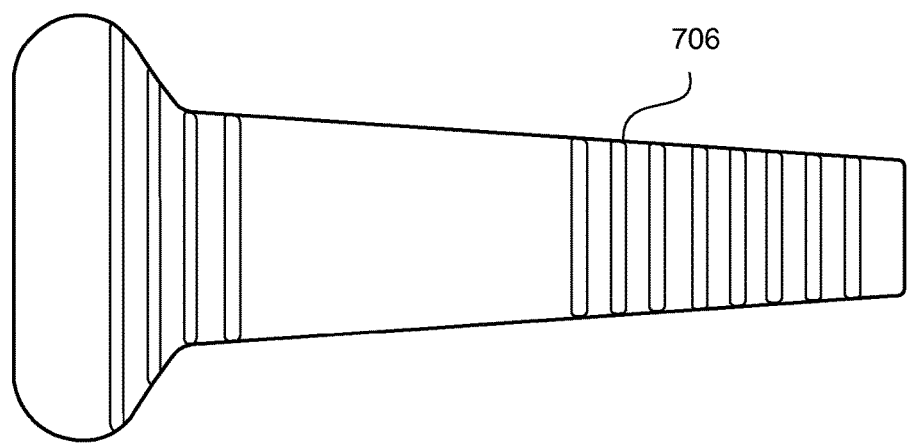
FIG. 7B illustrates a top view of the medical device of FIG. 7A according to an aspect.

FIGS. 7A and 7B illustrate a medical device 700 according to another aspect. FIG. 7A illustrates a side view of the medical device 700. FIG. 7B illustrates a top view of the medical device 700. The medical device 700 may be considered a re-usable medical delivery device since at least some of its components can be disassembled, sterilized, and then re-assembled for future use. Also, the medical device 700 may incorporate features and/or components described with reference to the previous figures. The medical device 700 may include a needle member 702 and a handle 706. In some examples, the needle member 702 and the handle 706 may be any of the needle members and handles with respect to any of the other figures described herein. In some aspects, the needle member 702 may be removably coupled to the handle 706 such that the needle member 702 and the handle 706 may be disassembled and re-assembled in order to allow the medical device 700 to be re-used. Furthermore, in some examples, the medical device 700 may also include any of the previously described pusher members. As such, the needle member 702 and the handle 706 may include previously described features that permit the medical device 700 to include a removable pusher member as previously described. The needle member 702 may include a coupling member 703 (e.g., a slot, L-shaped) configured to couple an implant. In some examples, the coupling member 703 may be disposed on the distal end portion of the needle member 702. The needle member 702 may include one or more curved portions. The needle member 702 may be removably coupled to the handle 706. The medical device 700 may include a fastening mechanism to removably couple the needle member 702 to the handle 706. In some examples, the needle member 702 may include a fastening member 705 configured to be coupled to the handle 706. In some examples, the fastening member 705 may be fixedly coupled to the proximal end portion of the needle member 702. In some examples, the fastening member 705 may be inserted into an opening or cavity of the handle 706. The handle 706 may include a secondary fastening member configured to be removably coupled to the fastening member 705. The secondary fastening member may be disposed within the opening or cavity of the handle 706. In some examples, the fastening member 705 may be a threaded (male or female) member to be coupled with a threaded (male or female) member of the handle 706. However, the medical device 700 may incorporate any type of fastening mechanism to removably couple the needle member 702 to the handle 706.

Figure 8:
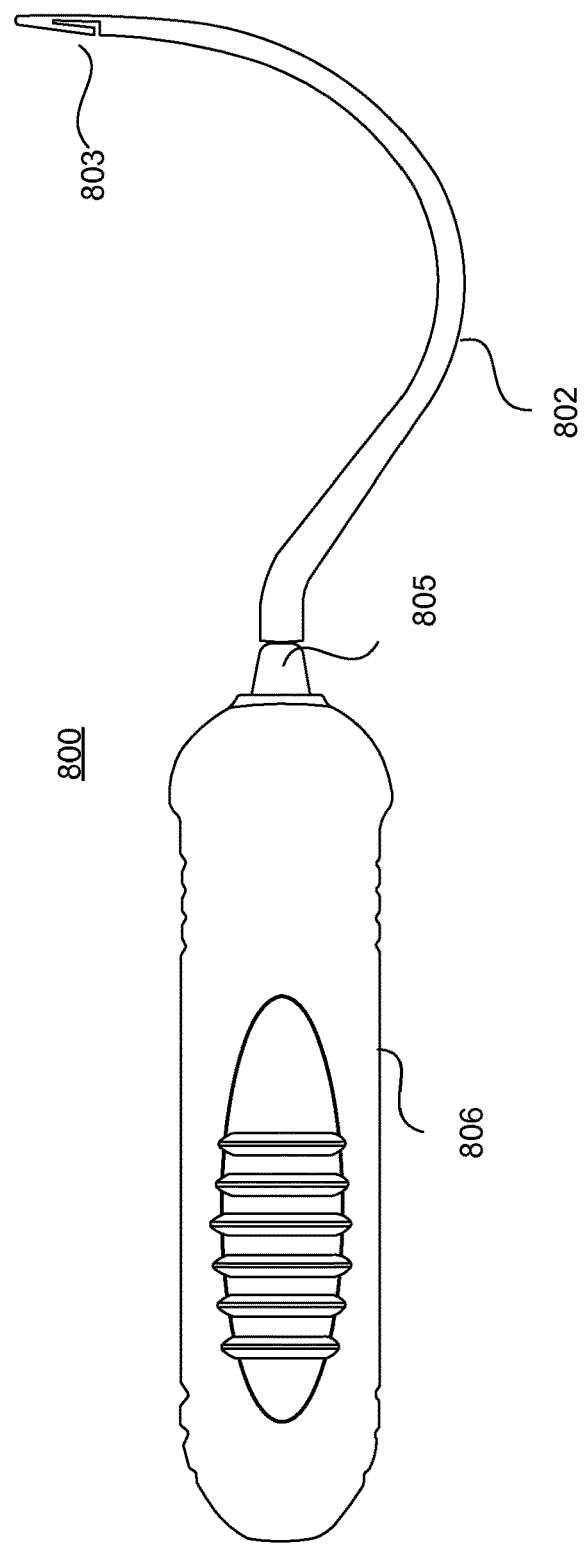
FIG. 8 illustrates a medical device according to another aspect.

FIG. 8 illustrates a medical device 800 according to another aspect. The medical device 800 may be considered a re-usable medical delivery device since at least some of its components can be disassembled, sterilized, and then re-assembled for future use. Also, the medical device 800 may incorporate features and/or components described with reference to the previous figures. The medical device 800 may include a needle member 802 and a handle 806. The needle member 802 may include a coupling member 803 (e.g., a slot, L-shaped) configured to couple an implant. In some examples, the coupling member 803 may be disposed on the distal end portion of the needle member 802. The needle member 802 may include one or more curved portions that may be different than the curvature of the needle member 702. The needle member 802 may be removably coupled to the handle 806. In some examples, the needle member 802 and the handle 806 may be any of the needle members and handles with respect to any of the other figures described herein. In some aspects, the needle member 802 may be removably coupled to the handle 806 such that the needle member 802 and the handle 806 may be disassembled and re-assembled in order to allow the medical device 800 to be re-used. Furthermore, in some examples, the medical device 800 may also include any of the previously described pusher members. As such, the needle member 802 and the handle 806 may include previously described features that permit the medical device 800 to include a removable pusher member as previously described. The medical device 800 may include a fastening mechanism to removably couple the needle member 802 to the handle 806. In some examples, the needle member 802 may include a fastening member 805 configured to be coupled to the handle 806. In some examples, the fastening member 805 may be fixedly coupled to the proximal end portion of the needle member 802. In some examples, the fastening member 805 may be inserted into an opening or cavity of the handle 806. The handle 806 may include a secondary fastening member configured to be removably coupled to the fastening member 805. The secondary fastening member may be disposed within the opening or cavity of the handle 806. In some examples, the fastening member 805 may be a threaded (male or female) member to be coupled with a threaded (male or female) member of the handle 806. However, the aspects incorporate any type of fastening mechanism to removably couple the needle member 802 to the handle 806.

Figure 9:
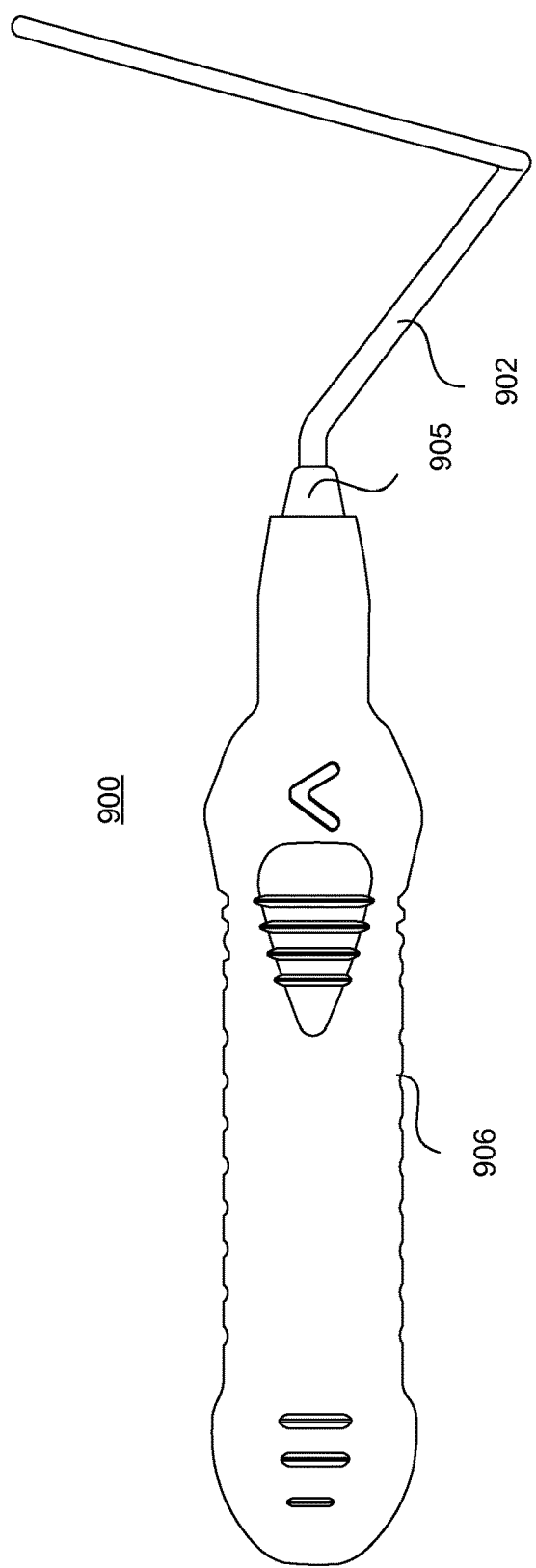
FIG. 9 illustrates a medical device according to another aspect.

FIG. 9 illustrates a medical device 900 according to another aspect. The medical device 900 may be considered a re-usable medical delivery device since at least some of its components can be disassembled, sterilized, and then re-assembled for future use. Also, the medical device 900 may incorporate features and/or components described with reference to the previous figures. The medical device 900 may include a needle member 902 and a handle 906. The needle member 902 may include one or more bent portions. The needle member 902 may be removably coupled to the handle 906. In some examples, the needle member 902 and the handle 906 may be any of the needle members and handles with respect to any of the other figures described herein. In some aspects, the needle member 902 may be removably coupled to the handle 906 such that the needle member 902 and the handle 906 may be disassembled and re-assembled in order to allow the medical device 900 to be re-used. Furthermore, in some examples, the medical device 900 may also include any of the previously described pusher members. As such, the needle member 902 and the handle 906 may include previously described features that permit the medical device 900 to include a removable pusher member as previously described. The medical device 900 may include a fastening mechanism to removably couple the needle member 902 to the handle 906. In some examples, the needle member 902 may include a fastening member 905 configured to be coupled to the handle 906. In some examples, the fastening member 905 may be fixedly coupled to the proximal end portion of the needle member 902. In some examples, the fastening member 905 may be inserted into an opening or cavity of the handle 906. The handle 906 may include a secondary fastening member configured to be removably coupled to the fastening member 905. The secondary fastening member may be disposed within the opening or cavity of the handle 906. In some examples, the fastening member 905 may be a threaded (male or female) member to be coupled with a threaded (male or female) member of the handle 906. However, the aspects incorporate any type of fastening mechanism to removably couple the needle member 902 to the handle 906.

Figure 10:
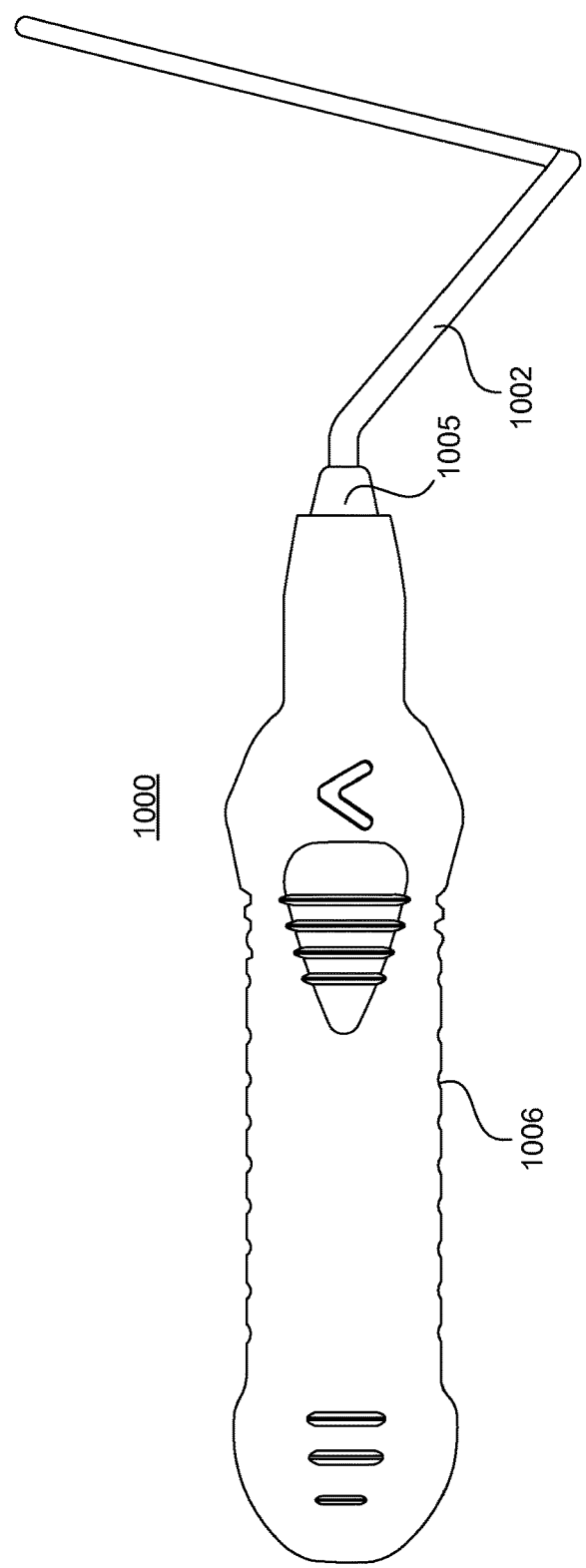
FIG. 10 illustrates a medical device according to another aspect.

FIG. 10 illustrates a medical device 1000 according to another aspect. The medical device 1000 may be considered a re-usable medical delivery device since at least some of its components can be disassembled, sterilized, and then re-assembled for future use. Also, the medical device 1000 may incorporate features and/or components described with reference to the previous figures. The medical device 1000 may include a needle member 1002 and a handle 1006. The needle member 1002 may include one or more bent portions. The needle member 1002 may be removably coupled to the handle 1006. In some examples, the needle member 1002 and the handle 1006 may be any of the needle members and handles with respect to any of the other figures described herein. In some aspects, the needle member 1002 may be removably coupled to the handle 1006 such that the needle member 1002 and the handle 1006 may be disassembled and re-assembled in order to allow the medical device 1000 to be re-used. Furthermore, in some examples, the medical device 1000 may also include any of the previously described pusher members. As such, the needle member 1002 and the handle 1006 may include previously described features that permit the medical device 1000 to include a removable pusher member as previously described. The medical device 1000 may include a fastening mechanism to removably couple the needle member 1002 to the handle 1006. In some examples, the needle member 1002 may include a fastening member 1005 configured to be coupled to the handle 1006. In some examples, the fastening member 1005 may be fixedly coupled to the proximal end portion of the needle member 1002. In some examples, the fastening member 905 may be inserted into an opening or cavity of the handle 1006. The handle 1006 may include a secondary fastening member configured to be removably coupled to the fastening member 1005. The secondary fastening member may be disposed within the opening or cavity of the handle 1006. In some examples, the fastening member 1005 may be a threaded (male or female) member to be coupled with a threaded (male or female) member of the handle 1006. However, the aspects incorporate any type of fastening mechanism to removably couple the needle member 1002 to the handle 1006.

Figure 11:
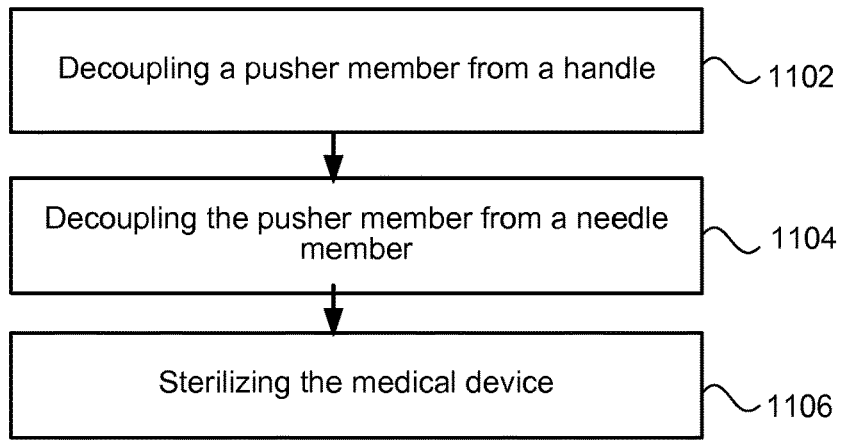
FIG. 11 illustrates a flow chart of a method for disassembling a medical device according to an aspect.

FIG. 11 illustrates a flowchart 1100 for a method of re-using a medical device according to an aspect. For example, after the medical device is used within a surgical procedure, the following steps may be performed to help to disassemble the medical device to permit the medical device to be re-used. The medical device may be any of the medical devices described herein. In some examples, the medical device may be the medical devices described in FIGS. 1-5. For example, the medical device may include a pusher member, a needle member, and a handle.

In step 1102, the pusher member may be de-coupled from the handle. In some examples, the pusher member may be de-coupled from the handle by rotating the pusher member as discussed in FIGS. 2A-2G. In some examples, the pusher member may move to the extended position. Then, the pusher member may rotate about its longitudinal axis. The rotation of the pusher member may cause the pusher member to be de-coupled from the handle.

In some examples, the pusher member may rotate off the handle through a slot defined on the pusher member. The slot may be disposed on a side portion of the extension member. In particular, the handle may define a track portion, and the extension member of the pusher member may be configured to be slidably disposed in the track portion. The extension member of the pusher member may define the slot. The track portion of the handle may define a recess to receive the extension member. Also, the handle may define a protrusion extending from the recess of the track portion. In some examples, the protrusion may extend from an end portion of the recess. Also, the extension member may define an opening that extends into the slot. The protrusion of the handle may be disposed within the opening of the extension member such that the protrusion limits the travel distance of the pusher member during the medical procedure when the extension member engages the protrusion. However, by rotating the pusher member, the protrusion of the handle moves through the slot of the extension member of the pusher member, thereby de-coupling the pusher member from the handle.

In some examples, the pusher member may be de-coupled from the handle by applying a pressure to a portion of the extension member of the pusher member, as described in FIGS. 3A-D. In some examples, the pusher may be de-coupled from the handle by applying a distal force greater than the force used to move the pusher member during the surgical procedure, as discussed in FIGS. 4A-C.

In step 1104, the pusher member may be decoupled from the needle member. In some examples, the pusher member may be decoupled from the needle member as described with reference to FIGS. 1-5. For example, the pusher member may define a slot or opening on the side of the pusher member, and the pusher member may be removed from the needle member through the slot or opening a direction different than an axis that defines the movement of the pusher during the medical procedure. In step 1106, the medical device may be sterilized such that the medical device can be re-assembled and then used in a subsequent medical procedure.

Figure 12:
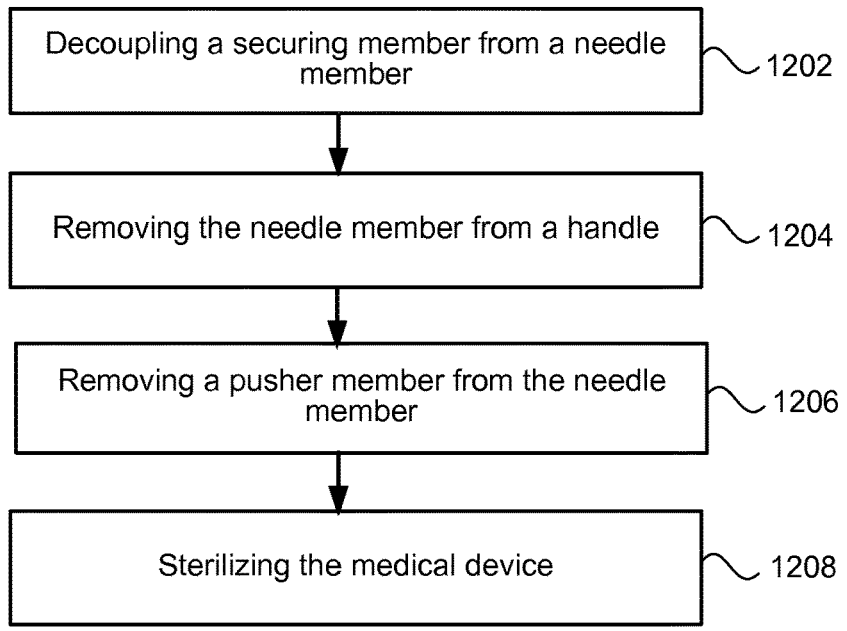
FIG. 12 illustrates a flow chart of a method for disassembling a medical device according to another aspect.

FIG. 12 illustrates a flowchart 1200 for a method of re-using a medical device according to an aspect. For example, after the medical device is used within a surgical procedure, the following steps may be performed to help to disassemble the medical device to permit the medical device to be re-used. The medical device may be any of the medical devices described herein. In some examples, the medical device may be the medical devices described in FIG. 6. For example, the medical device may include a pusher member, a needle member, a handle, and a securing member.

In step 1202, the securing member may be decoupled from the needle member. For example, the proximal end portion of the needle member may extend through a first opening of the handle into a cavity defined by the handle, the securing member may extend through a second opening of the handle into the cavity of the handle, and the securing member and the proximal end portion of the needle member may be removably coupled. In some examples, the securing member may be rotated to decouple the securing member from the proximal end portion of the needle member.

In step 1204, the needle member may be removed from the handle. For example, the proximal end portion of the needle member may move out of the first opening of the handle. In step 1206, the pusher member may be removed from the handle. For example, the pusher member may be slide over the proximal end portion of the needle member. In this manner, the pusher member, the needle member, and the handle may be separated. In step 1208, the medical device may be sterilized such that the medical device can be re-assembled and then used in a subsequent medical procedure.

In a general aspect, a medical device may include a needle member, and a handle coupled to the needle member. The handle may define a track portion. The medical device may also include a pusher member including a sheath defining a lumen configured to receive a portion of the needle member and an extension member being movably coupled to the track portion of the handle such that the pusher member is configured to move from a first position to a second position during a surgical procedure. The pusher member may be removable from the handle. The sheath may define a slot. The pusher member may be removable from the needle member through the slot or the lumen.

The track portion may define a recess, and at least a portion of the extension member is disposed within the recess. The track portion may include at least one protrusion. The track portion may include a tapered portion. The pusher member may be removable from the handle based on a rotation of the pusher member. The extension member may define a slot. The pusher member may be removable from the handle based on a rotation through the slot of the extension member. The extension member may include a flexible lip, and the pusher member is removable from the handle based on a force applied to the flexible lip. The pusher member may be removable from the handle by applying a force to the pusher member, where the force is greater than a force used to move the pusher member from the first position to the second position during the surgical procedure. The extension member may define a first extension member and a second extension member. The extension member may define an opening between the first extension member and the second extension member. The slot may extend in a direction parallel to a longitudinal axis of the pusher member. The pusher member may further include a handle portion. The handle portion may be disposed between the extension member and the sheath. The handle portion may be configured to be disposed around the portion of the needle member. The sheath and the handle portion define the slot. The handle portion may include a proximal end portion, where the extension member extends from a surface of the proximal end portion of the extension member. The handle defines a first opening, a second opening, and a lumen between the first opening and the second opening, where a proximal end portion of the needle member extends into the lumen through the first opening. The medical device may further include a securing member configured to be inserted into the lumen through the second opening of the handle. The securing member is configured to be removably coupled to the proximal end portion of the needle member. The proximal end portion of the needle member may include a first threaded fastener portion and the securing member may include a second threaded fastener portion.

According to another aspect, a medical device may include a needle member, a handle coupled to the needle member. The handle defines a track portion. The medical device may also include a pusher member including a sheath disposed around a portion of the needle member and an extension member being movably coupled to the track portion of the handle such that the pusher member is configured to move from a first position to a second position during a surgical procedure. The pusher member is removable from the handle. The sheath defines a slot. The pusher member is removable from the needle member through the slot. The track portion defines a recess, where at least a portion of the extension member is disposed within the recess. The track portion may include at least one protrusion. The track portion may include a tapered portion. The pusher member is removable from the handle based on a rotation of the pusher member. The extension member may define a slot, the pusher member is removable from the handle based on a rotation through the slot of the extension member. The extension member may include a flexible lip, and the pusher member is removable from the handle based on a force applied to the flexible lip. The pusher member may be removable from the handle by applying a force to the pusher member, where the force is greater than a force used to move the pusher member from the first position to the second position during the surgical procedure. The extension member may define a first extension member and a second extension member, where the extension member defines an opening between the first extension member and the second extension member. The slot may extend in a direction parallel to a longitudinal axis of the pusher member. The pusher member may further include a handle portion. The handle portion is disposed between the extension member and the sheath. The handle portion may be configured to be disposed around the portion of the needle member such that the sheath and the handle portion define the slot. The handle portion may include a proximal end portion, where the extension member extends from a surface of the proximal end portion of the extension member.

According to another aspect, a medical device may include a needle member having a proximal end portion, and a handle coupled to the proximal end portion of the needle member. The handle defines a track portion. The medical device may further include a pusher member including a sheath disposed around a portion of the needle member, a handle portion disposed around the portion of the needle member, and an extension member movably coupled to the track portion of the handle such that the pusher member is configured to move from a first position to a second position during a surgical procedure. The pusher member may be removable from the handle when not used within the surgical procedure. The sheath and the handle portion define a slot, and the pusher member is removable from the needle member through the slot. The track portion defines a recess, where at least a portion of the extension member is disposed within the recess. The handle portion includes a proximal end portion, where the extension member extends from a surface of the proximal end portion of the extension member. The slot may extend in a direction parallel to a longitudinal axis of the pusher member.

According to another aspect, a medical device may include a needle member having a proximal end portion, and a handle defining a first opening, a second opening, and a lumen between the first opening and the second opening. The proximal end portion of the needle member extends into the lumen through the first opening. The medical device may further include a securing member configured to be inserted into the lumen through the second opening of the handle. The securing member is configured to be removably coupled to the proximal end portion of the needle member. The medical device may further include a pusher member including a sheath disposed around a portion of the needle member, where the pusher member is configured to move from a first position to a second position in relation to the handle during a surgical procedure.

The pusher member may be removably coupled to the handle. The handle defines a track portion, and the pusher member includes an extension member. The extension member may be configured to be movably coupled to the track portion. The proximal end portion may include a first threaded fastener portion and the securing member may include a second threaded fastener portion.

While certain features of the described implementations have been illustrated as described herein, many modifications, substitutions, changes and equivalents will now occur to those skilled in the art. It is, therefore, to be understood that the appended claims are intended to cover all such modifications and changes as fall within the scope of the embodiments.

What is claimed is:
1. A medical device comprising:
 a needle member including a proximal end portion, a distal end portion, and an intermediate portion between the proximal end portion and the distal end portion, the proximal end portion having a first diameter and the intermediate portion having a second diameter, the second diameter being smaller than the first diameter;

a handle coupled to the proximal end portion of the needle member, the handle defining a track portion; and a pusher member including a sheath disposed around a portion of the needle member, a handle portion, and an extension member being movably coupled to the track portion of the handle such that the pusher member is configured to move from a first position to a second position during a surgical procedure, the extension member includes an elongated opening, the pusher member being removable from the handle, the sheath defining a slot, the pusher member being removable from the needle member through the slot.

2. The medical device of claim 1, wherein the track portion defines a recess, at least a portion of the extension member being disposed within the recess.

3. The medical device of claim 1, wherein the track portion includes at least one protrusion.

4. The medical device of claim 1, wherein the track portion includes a tapered portion.

5. The medical device of claim 1, wherein the pusher member is removable from the handle based on a rotation of the pusher member.

6. The medical device of claim 1, wherein the extension member defines a slot, the pusher member being removable from the handle based on a rotation through the slot of the extension member.

7. The medical device of claim 1, wherein the extension member includes a flexible lip, the pusher member being removable from the handle based on a force applied to the flexible lip.

8. The medical device of claim 1, wherein the pusher member is removable from the handle by applying a force to the pusher member, the force being greater than a force used to move the pusher member from the first position to the second position during the surgical procedure.

9. The medical device of claim 1, wherein the extension member defines a first extension member and a second extension member, the extension member defining the elongated opening between the first extension member and the second extension member.

10. The medical device of claim 1, wherein the slot extends in a direction parallel to a longitudinal axis of the pusher member.

11. The medical device of claim 1, wherein the handle portion is disposed between the extension member and the sheath, the handle portion configured to be disposed around the portion of the needle member, the sheath and the handle portion defining the slot.

12. The medical device of claim 11, wherein the handle portion includes a distal end portion, the extension member being coupled to the distal end portion of the handle portion.

13. A medical device comprising:

a needle member having a proximal end portion;

a handle coupled to the proximal end portion of the needle member, the handle defining a track portion; and a pusher member including a sheath disposed around a portion of the needle member, a handle portion disposed around the portion of the needle member, and an extension member movably coupled to the track portion of the handle such that the pusher member is configured to move from a first position to a second position during a surgical procedure, the extension member includes an opening on a surface of the extension member, the pusher member being removable from the handle when not used within the surgical procedure, the sheath and the handle portion defining a slot, the slot extending along a length of the sheath and the handle portion, the pusher member being removable from the needle member through the slot.

14. The medical device of claim 13, wherein the track portion defines a recess, at least a portion of the extension member being disposed within the recess.

15. The medical device of claim 13, wherein the handle portion includes a distal end portion, the extension member being coupled to the distal end portion of the handle portion.

16. The medical device of claim 13, wherein the slot extends in a direction parallel to a longitudinal axis of the pusher member.

17. A medical device comprising:

a needle member having a proximal end portion, a distal end portion, and an intermediate portion between the proximal end portion and the distal end portion, the proximal end portion having a first diameter and the intermediate portion having a second diameter, the second diameter being smaller than the first diameter;

a handle defining a first opening, a second opening, and a lumen between the first opening and the second opening, the proximal end portion of the needle member extending into the lumen through the first opening;

a securing member configured to be inserted into the lumen through the second opening of the handle, the securing member configured to be removably coupled to the proximal end portion of the needle member; and a pusher member including a sheath disposed around a portion of the needle member, a handle portion, and an extension member, the pusher member being configured to move from a first position to a second position in relation to the handle during a surgical procedure, the extension member includes an elongated opening.

18. The medical device of claim 17, wherein the pusher member is removably coupled to the handle.

19. The medical device of claim 17, wherein the handle defines a track portion, the extension member of the pusher member configured to be movably coupled to the track portion.

20. The medical device of claim 17, wherein the proximal end portion includes a first threaded fastener portion and the securing member includes a second threaded fastener portion.

* * * * *